United States Patent
Wolfe et al.

(10) Patent No.: US 7,291,488 B2
(45) Date of Patent: Nov. 6, 2007

(54) DETECTION OF HERPES SIMPLEX VIRUS TYPES 1 AND 2 BY NUCLEIC ACID AMPLIFICATION

(75) Inventors: David M. Wolfe, Red Lion, PA (US); Christine A. Martinaitis, Columbia, MD (US); Daretta A. Yursis, Parkton, MD (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 241 days.

(21) Appl. No.: 10/832,120

(22) Filed: Apr. 26, 2004

(65) Prior Publication Data

US 2005/0042601 A1   Feb. 24, 2005

Related U.S. Application Data

(60) Provisional application No. 60/465,458, filed on Apr. 25, 2003.

(51) Int. Cl.
   C12P 19/24   (2006.01)
   C07H 21/02   (2006.01)
   C07H 21/04   (2006.01)
   C12Q 1/68    (2006.01)

(52) U.S. Cl. .................. 435/91.2; 536/23.1; 435/6

(58) Field of Classification Search .................. None
   See application file for complete search history.

(56) References Cited

U.S. PATENT DOCUMENTS

| | | | |
|---|---|---|---|
| 5,270,184 A | 12/1993 | Walker et al. | |
| 5,455,166 A | 10/1995 | Walker | |
| 5,500,025 A | 3/1996 | Sharma | |
| 5,547,861 A | 8/1996 | Nadeau et al. | |
| 5,550,025 A | 8/1996 | Walker | |
| 5,593,867 A | 1/1997 | Walker et al. | |
| 5,648,211 A | 7/1997 | Fraiser et al. | |
| 5,846,726 A | 12/1998 | Nadeau et al. | |
| 5,888,739 A | 3/1999 | Pitner et al. | |
| 5,919,630 A | 7/1999 | Nadeau et al. | |
| 5,928,869 A | 7/1999 | Nadeau et al. | |
| 5,935,791 A | 8/1999 | Nadeau et al. | |
| 5,958,700 A | 9/1999 | Nadeau et al. | |
| 6,060,252 A | 5/2000 | Hellyer et al. | |
| 6,261,785 B1 | 7/2001 | Wood et al. | |
| 6,821,519 B2 * | 11/2004 | Day et al. ................ | 424/231.1 |

FOREIGN PATENT DOCUMENTS

EP   0 497 272 B1   10/1995

OTHER PUBLICATIONS

U.S. Appl. No. 09/652,126, filed Aug. 2000, Shyjan.*

Rekabdar et al., "Variability of the Glycoprotein G Gene in Clinical Isolates of Herpes Simplex Virus Type 1," *Clinical and Diagnostic Laboratory Immunology*, vol. 6, No. 6, pp. 826-831, Nov. 1999.
International Search Report for International Application No. PCT/US04/12766, date of completion of search: Feb. 14, 2005.
Ausubel et al., "Preparation and Analysis of DNA", *Current Protocols in Molecular Biology*, Suppls. 21, 26, 29, 35 and 42; pp. 2.10.7-2.10.16, 1994-1995.
Barany, "Genetic Disease Detection and DNA Amplification Using Cloned Thermistable Ligase", *Proc. Natl. Acad. Sci. USA*, 88:189-193, 1991.
Barringer et al., "Blunt-end and Single-strand Ligations by Escherichia coli Ligase: Influence on an in vitro Amplification Scheme", *Gene*, 89:117-122; 1990.
Guatelli et al., "Isothermal, in vitro Amplification of Nucleic Acids by a Multienzyme Reaction Modeled after Retroviral Replication", *Proc. Natl. Acad. Sci. USA*, 87:1874-1878, Mar. 1990.
Kimmel, "Identification and Characterization of Specific Clones: Strategy for Confirming the Validity of Presumptive Clones," *Methods in Enzymol*, 152:507-511, 1987.
Kwoh et al., "Transcription-based Amplification System and Detection of Amplified Human Immunodeficiency Virus Type 1 with a Bead-based Sandwich hybridization Format", *Proc. Natl. Acad. Sci. USA*, 86:1173-1177, Feb. 1989.
Lizardi et al., "Exponential Amplification of Recombinant-RNA Hybridization Probes" *BioTechnology*, 6:1197-1202, Oct. 1988.
Nadeau, et al., "Real-Time, Sequence-Specific Detection of Nucleic Acids During Strand Displacement Amplification", *Anal. Biochem*, 276: 177-187, 1999.
Saiki et al., "Enzymatic Amplification of β-Globin Genomic Sequences and Restriction site analysis for Diagnosis of Sickle Cell Anemia", *Science*, 230: 4732: 1350-1354, Dec. 20, 1985.
Walker et al., "Isothermal in vitro Amplification of DNA by a Restriction Enzyme/DNA Polymerase System", Proc. Natl. Acad. Sci. USA, 89: 392-396, Jan. 1992.
Walker et al., "Strand Displacement Amplification-an Isothermal, in vitro DNA Amplification Technique", *Nuc. Acids. Res.*, 20: 7, 1691-1696, 1992.
Wahl et al., "Molecular Hybridization of Immobolized Nucleic Acids: Theoretical Concept and Practical Considerations", *Methods Enzymol.*, 152: 399-407, 1987.
Wu et al., "The Ligation Amplification Reaction (LAR)-Amplification of Specific DNA Sequences Using Sequential Rounds of Template-Dependent Ligation", *Genomics*, 4:560-569, 1989.

* cited by examiner

*Primary Examiner*—Teresa E. Strzelecka
*Assistant Examiner*—Suchira Pande
(74) *Attorney, Agent, or Firm*—Morgan & Finnegan, LLP

(57) ABSTRACT

The present invention relates to a method of detecting the presence or absence of herpes simplex virus (HSV) in a sample based on amplifying a portion of the Glycoprotein G (US4) gene of HSV and detecting the presence of the amplified nucleic acid using primers and detector primers as described herewith. The method of the invention further identifies the type of HSV, either HSV-1 or HSV-2, in a sample. Also encompassed by the invention is a kit comprising the primers and detector primers which may be used with the amplification method described herewith.

47 Claims, 7 Drawing Sheets

FIG. 1

```
AAAAAGACCC CGACCCGCGT CTGTGGTGTT TTTGGCATCA TGTCGCCGGG  50
CGCCATGCGT GCCGTTGTTC CCATTATCCC ATTCCTTTTG GTTCTTGTCG 100
GTGTATCGGG GGTTCCCACC AACGTCTCCT CCACCACCCA ACCCCAACTC 150
CAGACCACCG GTCGTCCCTC GCATGAAGCC CCCAACATGA CCCAGACCGG 200
CACCACCGAC TCTCCCACCG CCATCAGCCT TACCACGCCC GACCACACAC 250
CCCCCATGCC AAGTATCGGA CTGGAGGAGG AGGA---AGA GGAGGAGGGG 300
GCCGGGGACG GCGAACATCT TGAGGGGGGA GATGGGACCC GTGACACCCT 350
ACCCCAGTCC CCGGGCCCAG CCTTCCCGTT GGCTGAGGAC GTCGAGAAGG 400
ACAAACCCAA CCGTCCCGTA GTCCCATCCC CCGATCCCAA CAACTCCCCC 450
GCGCGCCCCG AGACCAGTCG CCCGAAGACA CCCCCCACCA TTATCGGGCC 500
GCTGGCAACT CGCCCCACGA CCCGACTCAC CTCAAAGGGA CGACCCTTGG 550
TTCCGACGCC TCAACATACC CCGCTGTTCT CGTTCCTCAC TGCCTCCCCC 600
GCCCTGGACA CCCTCTTCGT CGTCAGCACC GTCATCCACA CCTTATCGTT 650
TTTGTGTATT GGTGCGATGG CGACACACCT GTGTGGCGGT TGGTCCAGAC 700
GCGGGCGACG CACACACCCT AGCGTGCGTT ACGTGTGCCT GCCGTCCGAA 750
CGCGGGTAG                                              759
```

FIG. 2

MOTA Algorithm

| Sample # | Dilution of Stock | | | | | |
|---|---|---|---|---|---|---|
| | 1:10 | 1:1000 | 1:10000 | Positive | Negative | Suspected laboratory contaminant |
| OSU 0-2021 | | | | | | |
| OSU 0-450 | | | | | | |
| OSU 0-1010 | | | | | | |
| OSU 0-2526 | | | | | | |
| OSU 0-1753 | | | | | | |
| OSU D-8-1973 | | | | | | |
| OSU 7-370 | | | | | | |
| OSU 0116-3 | | | | | | |
| OSU 1136 | | | | | | |
| OSU A.P. | | | | | | |
| ATCC VR-260 | | | | | | |
| ATCC VR-539 | | | | | | |
| DGX Clin1 | | | | | | |
| DGX Clin2 | | | | | | |
| DGX Clin3 | | | | | | |
| DGX Clin4 | | | | | | |
| DGX Clin5 | | | | | | |
| DGX Clin6 | | | | | | |
| DGX Clin7 | | | | | | |
| DGX Clin8 | | | | | | |
| DGX Clin9 | | | | | | |
| DGX Clin10 | | | | | | |
| DGX Clin19 | | | | | | |

```
CTCATGGCCT TGACCGAGGA CGCGTCCTCC GATTCGCCTA CGTCCGCTCC    50
GGAGAAGACG CCCCTCCCTG TGTCGGCCAC CGCCATGGCG CCCTCAGTCG   100
ACCCAAGCGC GGAACCGACC GCCCCCGCAA CCACTACTCC CCCCGACGAG   150
ATGGCCACAC AAGCCGCAAC GGTCGCCGTT ACGCCGGAGG AAACGGCAGT   200
CGCCTCCCCG CCCGCGACTG CATCCGTGGA GTCGTCGCCA CCCCCCGCCG   250
CGGCGGCAAC GCCCGGGGCC GGGCACACGA ACACCAGCAG CGCCTCCGCA   300
GCGAAAACGC CCCCCACCAC ACCAGCCCCC ACGACCCCCC CGCCCACGTC   350
TACCCACGCG ACCCCCCGCC CCACGACTCC GGGGCCCCAA ACAACCCCTC   400
CCGGACCCGC AACCCCGGGT CCGGTGGGCG CCTCCGCCGC GCCCACGGCC   450
GATTCCCCCC TCACCGCCTC GCCCCCCGCT ACCGCGCCGG GGCCCTCGGC   500
CGCCAACGTT TCGGTCGCCG CGACCACCGC CACGCCCGGA ACCGGGGCA    550
CCGCCCGTAC CCCCCCAACG GACCCAAAGA CGCACCCACA CGGACCCGCG   600
GACGCTCCCC CCGGCTCGCC AGCCCCCCCA CCCCCCGAAC ATCGCGGCGG   650
ACCCGAGGAG TTTGAGGGCG CCGGGGACGG CGAACCCCCC GAGGACGACG   700
ACAGCGCCAC CGGCCTCGCC TTCCGAACTC CGAACCCCAA CAAACCACCC   750
CCCGCGCGCC CCGGGCCCAT CCGCCCCACG CTCCCGCCAG GAATTCTTGG   800
GCCGCTCGCC CCCAACACGC CTCGCCCCCC CGCCAAGCT  CCCGCTAAGG   850
ACATGCCCTC GGGCCCCACA CCCCAACACA TCCCCCTGTT CTGGTTCCTA   900
ACGGCCTCCC CTGCTCTAGA TATCCTCTTT ATCATCAGCA CCACCATCCA   950
CACGGCGGCG TTCGTTTGTC TGGTCGCCTT GGCAGCACAA CTTTGGCGCG  1000
GCCGGGCGGG GCGCAGGCGA TACGCGCACC CGAGCGTGCG TTACGTATGT  1050
CTGCCACCCG AGCGGGATTA G                                 1071
```

FIG. 7

```
ACCACCCCCGGCGCGCCCATCCGCTCCCGGCCTCCGCCTCCGCCCCAACACGCCCTCGCCCCCCGCCCCAGCTCCCCTAAGGACATGCCCCTCGGGCCCCACACCC
TGGTGGGGGCCGCGGGAGGCGGAGGCGGTAGGCGAGGGTGCCGGGTTGCGGAGCGGGGGGTTCGAGGCGATTCCTGACGGCCCGGGGTGTGGG 780
                    └─BsoBI┘                                                              └─BsoBI┘  └─HSV2 LB┘
                              └─HSV2PCRL┘

CAACACATCCCCTGTTCTGGTTCCTAACGGCCCTCCCCCTGCTCTAGATATCCTCTCTTTATCATCAGCACCACCATCCACACGGCGGGGTTCGTTTGTCTCGGTCGCCTTGGCAGCACAACTTTGGCGGCC
GTTGTGTAGGGGACAAGACCAAGGATTGCCGGGAGGGGACGAGATCTATAGAGAAATAGTAGTCGTGGTGGTAGTTGTGCCGCCCAAGCAACAGACCAGCGGAACCGTCGTTGAAACCGCCGCCGG 910
└─HSV2 LB─┘                            └────HSV2 AD 2.0────┘              └─HSV2 AD 1.0─┘          └─HSV2 RP 1.1─┘   └─HSV2 RB 1.0─┘
      └─HSV2 LP 1.0─┘                                                                 └─HSV2 RP 5.2─┘    └─HSV2 RP 1.2─┘
                                                                                          └─HSV2 RP 2.0─┘

GGGCGGGGCGCAGGCGATACGGCCACCCCAGCGTGCCTTACGTATGTCTGCCACCCCAGCGGGATTAGGGGGTGGGGGTGGGGGTGTGGGGCGAGAGCGATGAAGGACGGAAAGGAACAGCGACCAAATGTCA
CCCGCCCCGCGTCCGCGTATGCCGGTGGGGTCGCAATGCATACAGACGGTGGGGTCGCCCTAATCCCCCACCCCCACCCCCGCTCTTTGCTACTTCCTGCCCCTTCCCTTGCTGGTTACAGT 1040
                          └─BsoBI┘                                                                                        └─HSV2 RP 1.0─┘
                              └─HSV2PCRR┘
```

DETECTION OF HERPES SIMPLEX VIRUS TYPES 1 AND 2 BY NUCLEIC ACID AMPLIFICATION

CROSS-REFERENCE TO RELATED APPLICATIONS

This application claims the benefit of Provisional Application No. 60/465,458, filed Apr. 25, 2003, entitled "Detection of Herpes Simplex 1 Virus by SDA" by David M. Wolfe.

FIELD OF THE INVENTION

The present invention relates to diagnostic methods and nucleic acid sequences for identifying Herpes Simplex Virus (HSV) by nucleic acid amplification methods.

BACKGROUND OF THE INVENTION

Herpes Simplex is an enveloped double-stranded DNA virus that is responsible for primary and recurrent infections in humans and is related to the viruses that cause infectious mononucleosis (Epstein-Barr Virus), chicken pox and shingles (Varicella Zoster Virus). Symptoms of Herpes Simplex Virus (HSV) infections include an eruption of tiny blisters on the skin or mucous membranes. After the eruption of blisters subsides, the virus remains in a dormant (latent) state inside the group of nerve cells (ganglia) that supply the nerve fibers to the infected area. Periodically, the virus reactivates, begins growing again, and travels through the nerve fibers back to the skin, thereby causing eruptions of blisters in the same area of skin as the earlier infection. Sometimes the virus may be present on the skin or mucous membranes even when there is no obvious blister. Herpes Simplex Virus (HSV) is classified into two types, HSV-1 and HSV-2. The complete genomes of human HSV-1 and HSV-2 have been sequenced (see, for example, NCBI Accession Nos. X14112 and Z86099, respectively).

HSV has been shown to contribute to or cause a variety of disorders, including blindness and encephalitis. Besides causing local outbreaks, HSV-1 and HSV-2 are associated with encephalitis. The pathophysiology of this encephalitis is poorly understood in humans. Animal models suggest that the virus enters the central nervous system through peripheral nerves and causes inflammation of the brain. HSV-1 is the more common cause of adult encephalitis. HSV-2 is the more common cause of newborn encephalitis, which is associated with maternal genital infections. HSV-2 is one of the most common sexually transmitted diseases in society. HSV-related encephalitis has the highest fatality rate of all the types of encephalitis with an annual incidence of 1 to 4 per million. HSV encephalitis affects people of all ages and at any time of the year. In adults, HSV-related encephalitis is thought to be due to a reactivation of a latent virus. Symptoms may include fever, headaches, seizures, an altered level of consciousness and personality changes. The similarity of these symptoms to other maladies makes clinical diagnosis difficult. If left untreated, the mortality rate for herpes simplex encephalitis (HSE) is as high as seventy percent, compared with as low as nineteen percent among those who receive treatment. Of the treated patients, approximately thirty-eight percent are reported to eventually return to normal function. It is, therefore, very important to be able to diagnose HSV infection at an early stage.

The diagnosis of HSV infection is commonly performed using cell culture on appropriate clinical specimens. However, the ability to isolate HSV in cell culture is reduced in old lesions, in the presence of a host immune response and in episodes of reactivation. Serologic diagnosis, particularly of HSV in cerebrospinal fluid (CSF), is not sufficiently sensitive or specific, and takes too much time to be of use in decisions involving choices for early therapeutic intervention of encephalitis. HSV is rarely detected in cerebral spinal fluid using cell culture, with only four percent of the cases being culture-positive. Serological methods are also inadequate for diagnosis of HSE due to delay between two and three weeks in appearance of antibody response after initial infection. The "gold standard" method of diagnosis involving brain biopsies is invasive and controversial with significant risk of long-term morbidity. Alternate techniques such as Computer-Assisted Tomography and Magnetic Resonance Imaging are not specific and lack sensitivity as diagnostic tools.

At the present time, immunological methods for detection of HSV are unreliable and difficult to perform. Molecular methods of detection offer the potential for enhanced sensitivity and faster time to result than is possible by conventional means. There are instances in which rapid, sensitive, and specific diagnosis of HSV disease is imperative. There is therefore, a clinical need to develop a rapid and sensitive tool to aid in the diagnosis of HSV. There also remains a need for a tool for the typing of the HSV infection. Rapid identification of the specific etiological agent involved in a viral infection provides information which can be used to determine appropriate therapy within a short period of time.

SUMMARY OF THE INVENTION

The present invention relates to methods and compositions for determining the presence of Herpes Simplex Virus (HSV), specifically Herpes Simplex Virus type 1 (HSV-1) or type 2 (HSV-2) in mammals. The method involves using primers to amplify and detect Herpes Simplex Virus target sequence. One embodiment uses the amplification technique of Strand Displacement Amplification (SDA).

The nucleic acid primers of the invention uniquely amplify the target sequence in HSV-1 or HSV-2, thereby allowing sensitive detection and type-identification of HSV. The present invention is also directed to a Strand Displacement Amplification (SDA) based method for the detection of HSV that involves real-time detection using a universal fluorescent energy transfer probe. The probes and primers of the present invention provide a direct, rapid, and sensitive detection of HSV nucleic acids and therefore offer an attractive alternative to immunological assays.

The probes and primers of the invention may be used after culture of the sample as a means for confirming the identity of the cultured organism. Alternatively, they may be used prior to culture or in place of culture for detection and identification of HSV nucleic acids using known amplification methods. The inventive probes, primers, and compositions and assay methods using the probes, primers, and compositions, provide a means for rapidly discriminating between the nucleic acid target sequences of HSV-1 and HSV-2, allowing the practitioner to identify, diagnose, and treat the HSV type without resorting to the time-consuming immunological and biochemical procedures typically relied upon.

BRIEF DESCRIPTION OF THE DRAWINGS

The various objects, advantages and novel features of the present invention will be readily understood from the following detailed description when read in conjunction with the appended drawings in which:

FIG. 1 shows a consensus sequence (SEQ ID NO: 1) of the Glycoprotein G (US4) gene of Herpes Simplex Virus Type 1 (HSV-1).

FIG. 2 is a map showing a portion of the genomic sequence of the HSV-1 target region (SEQ ID NO: 2) and the location of primers, bumpers, and adapters designed for specific detection of HSV-1 DNA.

FIG. 5 depicts the analytical sensitivity of the SDA method on dilutions of various HSV-1 strains.

FIG. 6 is a consensus sequence (SEQ ID NO: 3) of a fragment of the Glycoprotein G (US4) gene of Herpes Simplex Virus Type 2 (HSV-2).

FIG. 7 is a map showing the genomic sequence of the HSV-2 target region (SEQ ID NO: 4) and the location of primers, bumpers, and adapters designed for specific detection of HSV-2 DNA.

DETAILED DESCRIPTION OF THE INVENTION

Figure 3:
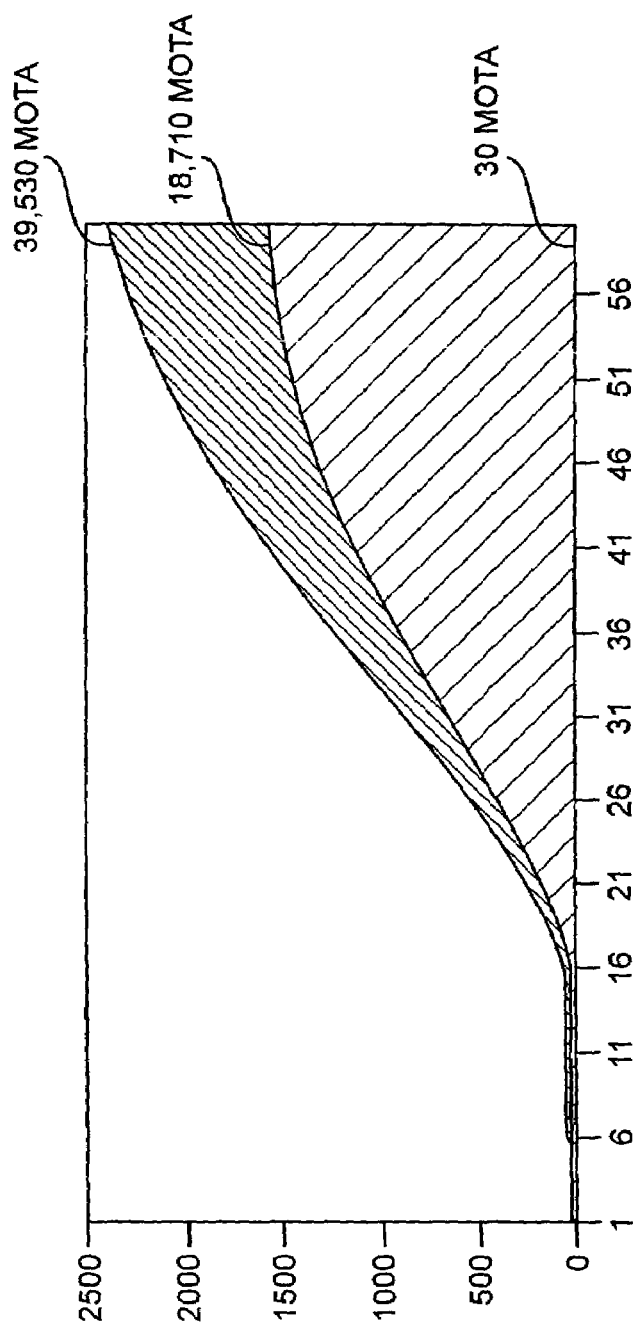
FIG. 3 is a graph showing "MOTA" expression of results.

The present invention provides isolated and purified nucleic acids, polynucleotides, amplification primers and assay probes which exhibit Herpes Simplex Virus (HSV) type specificity in nucleic acid amplification reactions. Also provided are methods for detecting and identifying HSV nucleic acids using the probes and primers of the invention.

One embodiment of the present invention relates to an amplification method for detecting the presence of a target nucleic acid sequence using one or more amplification primers having a target binding sequence, producing an amplified target sequence, and detecting the target sequence. Non-limiting examples of amplification methods include Polymerase Chain Reaction (PCR; see Saiki et al., 1985, *Science* 230:1350-1354, herein incorporated by reference), Ligase Chain Reaction (LCR; see Wu et al., 1989, *Genomics* 4:560-569; Barringer et al., 1990, *Gene* 89:117-122; Barany, 1991, *Proc. Natl. Acad. Sci. USA* 88:189-193, all of which are incorporated herein by reference), in situ hybridization, Transcription Mediated Amplification (TMA; see Kwoh et al., 1989, *Proc. Natl. Acad. Sci. USA* 86:1173-1177, herein incorporated by reference), Self-Sustaining Sequence Replication (3SR; see Guatelli et al., 1990, *Proc. Natl. Acad. Sci. USA* 87:1874-1878, herein incorporated by reference), Rolling Circle Amplification (RCA), Nucleic Acid Sequence Based Amplification (NASBA), Qβ replicase system (Lizardi et al., 1988, *BioTechnology* 6:1197-1202, herein incorporated by reference) and Strand Displacement Amplification (SDA; see Walker et al., 1992, *Proc. Natl. Acad. Sci. USA* 89:392-396; Walker et al., 1992, *Nuc. Acids. Res.* 20:1691-1696; and EP 0 497 272, all of which are incorporated herein by reference)) including thermophilic SDA (tSDA).

Another embodiment of the present invention relates to an isothermal Strand Displacement Amplification (SDA) method for detecting the presence of HSV nucleic acid sequences in a sample by exponential amplification of the HSV target sequence. In a further embodiment, SDA is performed at about 52° C. as described in U.S. Pat. No. 5,648,211 using a selected detector primer to detect a target during amplification as described in U.S. Pat. Nos. 5,919,630; 5,928,869; 5,958,700; and 6,261,785, all of which are hereby incorporated by reference. As typical with SDA, reagents, primers, enzymes, such as restriction enzymes and polymerase, and other components are added to a reaction microwell, container, or receptacle. SDA amplifies a specific DNA sequence from a sample, where once all the components are mixed together, the reaction continues until a critical component is exhausted. In contrast to the polymerase chain reaction (PCR), SDA is an isothermal reaction process such that, once the reaction is initiated, there is no external control over the progress of the reaction.

The SDA method of the present invention requires at least two HSV amplification primers and two bumper primers to initiate the amplification method. The amplification primers are designed to be highly specific for HSV-1 or HSV-2. The SDA method involves concurrent amplification reactions in a mixture and does not require separate phases or cycles for temperature cycling as is necessary in a PCR amplification method. A further advantage of the SDA of the present invention is exponential amplification. The steps of DNA polymerase extension, nicking, displacement, and regeneration of the nick site result in displaced single-stranded molecules with partial restriction enzyme sites (e.g., BsoBI sites) at either end which then circulate and are captured by amplification primers, thereby exponentially amplifying the HSV target sequence. The SDA method also provides an improved workflow, especially for high-throughput methods. SDA may be incorporated in a microarray-based application, where small volume amounts (nanoliters) of sample and reagents may be used to amplify HSV target DNA and detect the amplification products on a microchip array by performing multiple SDA assays on a single platform. The primary advantage of the SDA method for detecting HSV in a sample is the minimal labor requirement and high-throughput potential since the isothermal amplification process presents significantly fewer technical challenges in design and maintenance of the platform.

Figure 2:
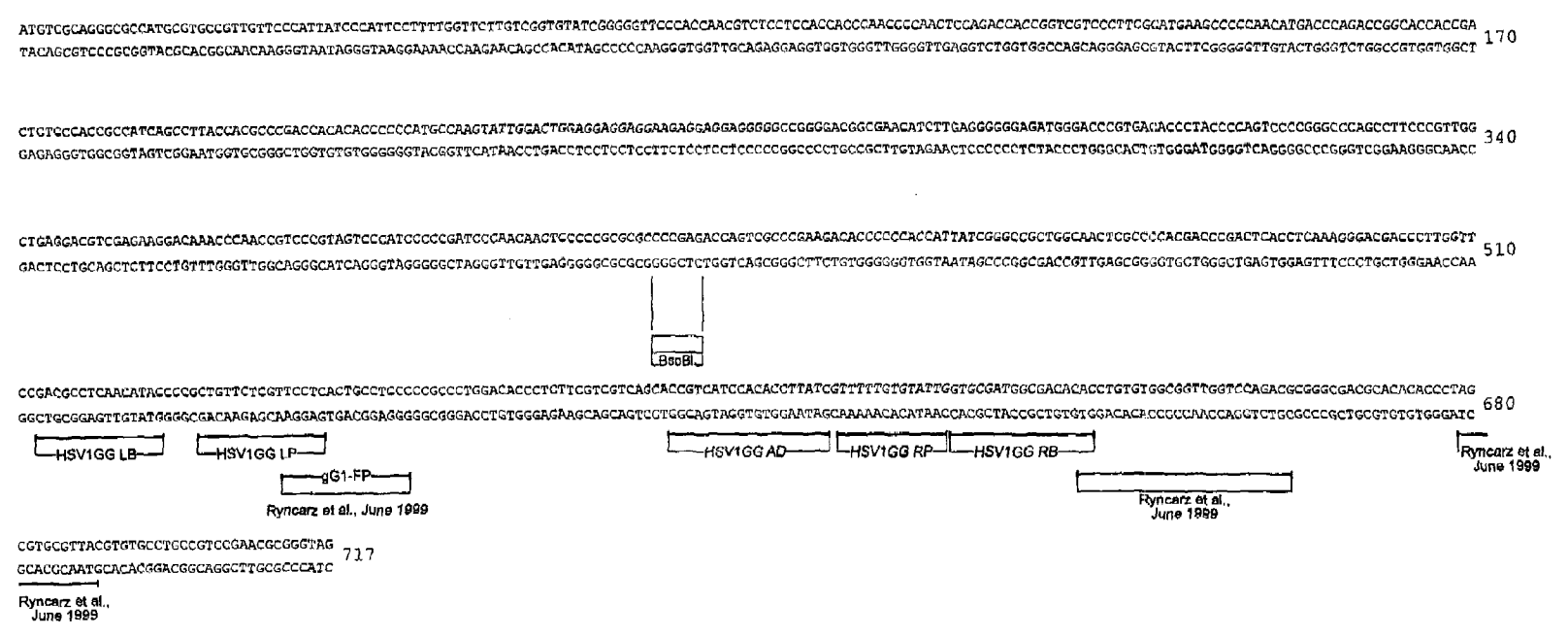

The term "target" or "target sequence," as used herein, refers to HSV nucleic acid sequences, HSV-1 or HSV-2, to be amplified and detected. These include the original HSV nucleic acid sequence to be amplified, the complementary second strand of the original HSV nucleic acid sequence to be amplified, and either strand of a copy of the original HSV sequence which is produced by the amplification reaction. These copies serve as amplifiable targets since they contain copies of the sequence to which the amplification primers anneal. Copies of the target sequence which are generated during the amplification reaction are referred to as amplification products, amplimers or amplicons. The HSV-1 and HSV-2 target sequences are located in the Glycoprotein G (US4) gene of the HSV-1 and HSV-2 genomic sequences. The HSV-1 target sequence is located between bases 555 and 680 of the consensus sequence of FIG. 1. The HSV-2 target sequence is located between bases 867 and 990 of the consensus sequence of FIG. 6. The Glycoprotein G (US4) gene is located between position 136,744 and 137,460 of the HSV-1 genomic sequence and between positions 137,878 to 139,977 of the HSV-2 genomic sequence of FIGS. 2 and 7, respectively.

As used herein, an "amplification primer" is a primer that anneals to a target sequence and can be extended by amplification. The region of the amplification primer that binds to the target sequence is the target binding sequence. Amplification techniques include, but are not limited to, Strand Displacement Amplification (SDA), including thermophilic SDA (tSDA), Polymerase Chain Reaction (PCR), Ligase Chain Reaction (LCR), in situ hybridization, Self-Sustaining Sequence Replication (3SR), Rolling Circle Amplification (RCA), Nucleic Acid Sequence Based Amplification (NASBA), And Transcription Mediated Amplification (TMA).

In one embodiment, an amplification primer may be used in a Strand Displacement Amplification (SDA) method. The amplification primer comprises at the 3' end, a target binding sequence portion which binds to the HSV target sequence, and at the 5' end, a portion that does not bind or anneal to the target sequence. The portion of the SDA amplification primer that does not bind the target sequence also comprises a tail and a recognition site for a restriction endonuclease upstream of the target binding sequence as described in U.S. Pat. No. 5,455,166 and U.S. Pat. No. 5,270,184, incorporated herein by reference. This recognition site is specific for a restriction endonuclease which will nick one strand of a DNA duplex when the recognition site is hemimodified, as described by Walker, et al. (1992. *Proc. Natl. Acad. Sci. USA* 89:392-396 and 1992 *Nucl. Acids Res.* 20:1691-1696). The tail is upstream of the restriction endonuclease recognition site sequence and functions as a polymerase repriming site when the remainder of the amplification primer is nicked and displaced during SDA. The repriming function of the tail sustains the SDA reaction and allows synthesis of multiple amplicons from a single target molecule. The length and sequence of the tail are generally not critical and can be routinely selected and modified.

One embodiment of the invention is based on the target binding sequence conferring target specificity on the amplification primer, where it should be understood that the target binding sequences exemplified in the present invention may also be used in a variety of other ways for detection of HSV. For example, the target binding sequences disclosed herein may alternatively be used as hybridization probes for direct detection of HSV, either without prior amplification or in a post-amplification assay. Such hybridization methods are well known in the art and typically employ a detectable label associated with or linked to the target binding sequence to facilitate detection of hybridization. Furthermore, Tables 1 and 2 list primer sequences (SEQ ID NOs: 5-25 and 36-47, respectively) containing a target binding sequence which is indicated by capitalization and underlining. These target binding sequences may be used as primers in amplification reactions which do not require additional specialized sequences (such as, PCR) or appended to the appropriate specialized sequences for use in NASBA, in situ hybridization, TMA, 3SR, other transcription based amplification primers which require an RNA polymerase promoter linked to the target binding sequence of the primer, or any other primer extension amplification reactions. These amplification methods which require specialized non-target binding sequences in the primer are necessary for the amplification reaction to proceed and typically serve to append the specialized sequence to the target. For example, the restriction enzyme recognition site is necessary for exponential amplification to occur in SDA (see U.S. Pat. Nos. 5,455,166 and 5,270,184). Amplification primers for Self-sustained Sequence Replication (3SR) and Nucleic Acid Sequence-Based Amplification (NASBA), in contrast, comprise an RNA polymerase promoter near the 5' end. (3SR assays are described in Guatelli et al., 1990, Proc. Natl. Acad. Sci. USA 87:1874-1878) The promoter is appended to the target binding sequence and serves to drive the amplification reaction by directing transcription of multiple RNA copies of the template. Linking such specialized sequences to a target binding sequence for use in a selected amplification reaction is routine and well known to one of ordinary skill in the art.

In contrast, amplification methods such as PCR, which do not require specialized sequences at the ends of the target, generally employ amplification primers consisting of only target binding sequence. For detection purposes in these other amplification methods, the primers may be detectably labeled as understood by the skilled artisan.

As nucleic acids do not require complete complementarity in order to anneal, one skilled in the art would understand that the probe and primer sequences disclosed herein may be modified to some extent without loss of utility as HSV-1-and HSV-2-specific primers and probes. The term "homology" refers to a degree of complementarity. There may be partial homology or complete homology, wherein complete homology is equivalent to identity. A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction.

As will be understood by those of skill in the art, the stringency of annealing may be altered in order to identify or detect identical or related polynucleotide sequences. As will be further appreciated by the skilled practitioner, the melting temperature, $T_m$, may be approximated by the formulas as known in the art, depending on a number of parameters, such as the length of the primer or probe in number of nucleotides, or annealing buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.* 152:507-511). As a general guide, $T_m$ decreases approximately 1° C.-1.5° C. with every 1% decrease in sequence homology. Temperature ranges may vary between about 50° C. and 62° C., but the amplification primers may be designed to be optimal at 52° C. However, temperatures below 50° C. may result in primers lacking specificity, while temperatures over 62° C. may result in no hybridization. A further consideration when designing amplification primers is the guanine and cytosine content. Generally, the GC content for a primer may be about 60-70%, but may also be less and can be adjusted appropriately by one skilled in the art. The hybridizing region of the target binding sequence may have a $T_m$ of about 42° C.-48° C. Annealing complementary and partially complementary nucleic acid sequences may be obtained by modifying annealing conditions to increase or decrease stringency (i.e., adjusting annealing temperature or salt content of the buffer). Such minor modifications of the disclosed sequences and any necessary adjustments of annealing conditions to maintain HSV-1 and HSV-2 specificity require only routine experimentation and are within the ordinary skill in the art.

The amplification primers designed for detection of HSV-1 and HSV-2 target sequences are identified in Tables 1 and 2 as SEQ ID NOs: 7-18 and 38-43, respectively. These amplification primers are designed such that the target binding sequence anneals to a segment of the highly homologous consensus Glycoprotein G (US4) gene region (see, FIGS. 1-2 and 6-7). HSV target binding sequence regions within the amplification primers that anneal to or are complementary to HSV target DNA sequences, are underlined and capitalized (see, Tables 1 and 2). The remaining 5' portion of the SDA detection primer sequences comprises the BsoBI restriction endonuclease recognition site (RERS) (as indicated in lowercase italics) that is required for the SDA reaction to proceed, as well as, a generic non-target-specific 5' tail end sequence.

HSV-1 and HSV-2 amplification primers of SEQ ID NOs: 7-8 and 38, respectively, are left hand ("first") S1 amplification primers, and SEQ ID NOs: 9-18 and 39-43, respectively, are right hand ("second") S2 amplification primers. For amplification purposes, a pair of HSV amplification primers of a specific type may be used alone (i.e., one HSV-1 left amplification primer and one HSV-1 right amplification primer) or in combination (i.e., one HSV-1 SDA left primer and two HSV-1 SDA right primers), such that there is at least one left and right hand primer pair in the reaction. Multiple amplification primers may be used to amplify several regions of the target sequence. The concentrations of primers may be adjusted appropriately, such that when an HSV-1 first amplification primer is used as the sole first amplification primer at a concentration of 500 nM, two HSV-1 right amplification primers may be used in conjunction, each have a concentration of 250 nM.

The term "extension product" generally refers to the sequence produced by extending a primer or target sequence using an enzyme, such as polymerase. In one embodiment, hybridization of an amplification primer and extension of the amplification primer by polymerase using the HSV target sequence as a template produces an amplification primer extension product.

A "bumper primer" or "external primer" is a primer that anneals to a target sequence upstream of the amplification primer such that extension of the bumper primer displaces the downstream amplification primer and its extension product. As used herein, the term "bumper primer" refers to a polynucleotide comprising an HSV target binding sequence. Useful bumper primers are identified in Tables 1 and 2 as SEQ ID NOs: 23-25 and 46-47, respectively. The left or first HSV-1 and HSV-2 bumper primers are SEQ ID NOs: 23 and 46, respectively, while the right or second HSV-1 and HSV-2 bumper primers are SEQ ID NOs: 24-25 and 47, respectively. Bumper primers are derived from conserved regions of sequence that flank the amplification primers at a position upstream of the amplification primers that is sufficiently close to the target binding site of the amplification primer to allow displacement of the amplification primer extension product after extension of the bumper primer. For example, the 5' end of the HSV-1 first bumper primer of SEQ ID NO: 23 (HSV1GGLB1.0) is located at base 137,256 of the HSV-1 genomic sequence (FIG. 2). The 5' end of the HSV-1 second bumper primer of SEQ ID NO: 25 (HSV1GGRB1.1) is located at base 137,382 of the HSV-1 genomic sequence (FIG. 2). During the initial round of SDA, the bumper primers hybridize to the HSV target sequence and displace by polymerase extension, the downstream amplification primer extension products, resulting in the generation of a single-stranded DNA that may undergo further rounds of replication and/or exponential amplification.

The term "assay probe" refers to any nucleic acid used to facilitate detection or identification of a nucleic acid. For example, in an embodiment of the present invention, assay probes are used for detection or identification of HSV nucleic acids. Detector probes, detector primers, capture probes and primers as described below are examples of assay probes.

In particular, "detector probes" useful in detecting and identifying specific HSV-types are labeled or tagged. The detectable label of the detector probe is a moiety that may be detected either directly or indirectly, indicating the presence of the target nucleic acid sequence. For direct detection, the assay or detector probe may be tagged with a radioisotope and detected by autoradiography or tagged with a fluorescent moiety and detected by fluorescence as known in the art. Alternatively, the assay probes may be indirectly detected by labeling with additional reagents that enable the detection. Indirectly detectable labels include, for example, chemiluminescent agents, enzymes that produce visible or colored reaction products, and a ligand-detectably labeled ligand binding partner, where a ligand (e.g., haptens, antibodies, or antigens) may be detected by binding to labeled ligand-specific binding partner.

For detection of the amplification products, amplification primers comprising the target binding sequences disclosed herein may be labeled as is known in the art, or labeled detector primers comprising the disclosed target binding sequences may be used in conjunction with the amplification primers as described in U.S. Pat. Nos. 5,547,861; 5,928,869; 5,593,867; 5,550,025; 5,935,791; 5,888,739; 5,846,726 for real-time homogeneous detection of amplification. Such detector primers may comprise a directly or indirectly detectable sequence which does not initially hybridize to the target but which facilitates detection of the detector primer once it has hybridized to the target and been extended. For example, such detectable sequences may be sequences which contain a restriction site, or sequences which form a secondary structure which brings fluorophore and quencher moieties in close proximity, such as, but not limited to hairpin and g-quartet sequences, or linear sequences which are detected by hybridization of their complements to a labeled oligonucleotide (sometimes referred to as a reporter probe) as is known in the art. Alternatively, the amplification products may be detected either in real-time or post-amplification through the use of intercalating dyes or post-amplification by hybridization of a probe selected from any of the target binding sequences disclosed herein which fall between a selected set of amplification primers.

Terminal and internal labeling methods are known in the art and may be used to link the donor and acceptor dyes at their respective sites in the detector primer. Examples of 5'-terminal labeling methods include a) periodate oxidation of a 5'-to-5' coupled ribonucleotide followed by reaction with an amine-containing label, b) condensation of ethylenediamine with a 5'-phosphorylated polynucleotide followed by reaction with an amine-reactive label, and c) introduction of an aliphatic amine substituent using an aminohexyl phosphite reagent in solid-phase DNA synthesis followed by reaction with an amine-reactive label. Labels may also be linked to synthetic DNA oligonucleotides at specific locations using special aliphatic amine-containing nucleotide phosphoramidite reagents. Selection of an appropriate method for linking the selected labels to the detector primer and performing the linking reactions are routine in the art.

Another embodiment utilizes a detector primer that hybridizes to a specific target sequence resulting in the necessity for multiple detector primers depending on the target sequence being detected. However, an embodiment for the detection and identification of the specific HSV-type uses the Universal detection system, which is modified from the real-time SDA detection method described by Nadeau, et al. (1999). The Universal detection system permits the use of the same pair of fluorescent detector primers for multiple assays, offering several advantages such as cost, time, and reduced technical complexity.

"Signal" or "adapter" primers have a target binding portion that hybridizes to the HSV target sequence and a tail portion that is generic and does not bind to the HSV target sequence. Adapter primers are used in conjunction with detector primers for Universal detection. The detector primer hybridizes to the tail portion (i.e., the non-target binding sequence) of the complement adapter primer. Signal or adapter primers are designed to hybridize to regions of the target sequence that lie at least partially in the intervening region between the first and second amplification primers so that the signal or adapter primers are displaced during the amplification reaction. HSV-1 and HSV-2 signal or adapter primers having SEQ ID NOs: 19-22 and 44-45 are shown in Tables 1 and 2, respectively.

The detector probe may be a "universal detector primer" or "detector primer" which has a 5' tail end portion that is detectably labeled and a 3' end portion which binds to the complement adapter primer tail sequence. Generally, the 3' end of the detector primer does not contain sequences with any significant complementarity to the HSV or Internal Amplification Control (IAC) target sequence. The detector primer also has a restriction enzyme recognition site at the 5' end.

Briefly, this Universal detection system can be used simultaneously and in the same reaction container as the SDA method for amplification. The Universal detection system involves the target-dependent extension of an unlabeled adapter primer. The adapter primer comprises an HSV-1 or HSV-2 target specific 3' sequence and 5' generic tail and is exemplified in SEQ ID NOs: 19-22 and SEQ ID NOs: 44-45, and its complement, respectively. The adapter primer hybridizes to the amplified HSV target sequence downstream of the S1 amplification primer. DNA polymerase extends from the 3' ends of the adapter primer and the S1 amplification primer, where the extension of the amplification primer displaces the adapter primer extension product. The S2 amplification primer anneals to the adapter primer extension product. DNA polymerase extends the 3' end of the S2 amplification primer, producing a double-stranded molecule comprising the adapter primer extension product and its complement, and has a nickable restriction enzyme recognition site. Nicking refers to breaking the phosphodiester bond of only one of two strands in a DNA duplex. A corresponding restriction enzyme nicks the double-stranded molecule at the restriction enzyme recognition site creating a 5' portion comprising a short nicked tail and a 3' portion comprising a long nicked complement adapter primer extension product. Nicking the restriction enzyme site with a corresponding restriction enzyme, such as, BsoBI enzyme, and extending the strand from the nicked site displaces a single-stranded copy of the adapter primer complement. DNA polymerase extends the 3' end of the nicked tail, thereby displacing the single-stranded nicked complement adapter primer extension product. The S1 amplification primer extension product and extended HSV target sequence may be further amplified exponentially by SDA. The displaced complement adapter primer extension product is then captured by a detector primer, where the 3' end of the detector primer anneals to the 5' portion of the complement adapter primer extension product. The detector primer comprises a detectable label and detects target sequence. DNA polymerase extension from the 3' ends of the detector primer and the complement adapter primer extension product results in opening the hairpin, if present, producing a double-stranded detection molecule comprising a detector primer extension product and its complement. Each strand comprises a cleavable restriction enzyme recognition site, which when cleaved separates the donor and quencher dyes, separating the fluorophore and the quencher moieties, and generating target-specific fluorescence. Due to the separation, the quencher is no longer capable of suppressing the fluorescence emitted by the fluorophore. Complete cleavage of the double-stranded detector primer restriction enzyme recognition site increases the fluorescent signal by separating the fluorophore and quencher.

In an embodiment of the invention, detector primers may be tagged for fluorescence detection with a fluorescent donor moiety (or fluorophore) and a quencher moiety where each moiety flanks the restriction enzyme recognition site. Tables 1 and 2 show detector primer sequences having SEQ ID NOs: 30-35. In Universal detection, the detector primers for detecting target sequence are generally used in conjunction with adapter primers. Detector primers that are labeled with a donor dye, rhodamine (ROX™), and a quencher dye, P-(dimethyl aminophenylazo) benzoic acid (DABCYL™) having SEQ ID NOs: 30-33 are used for HSV target sequence detection in an embodiment of the invention. Other donor and quencher dye pairs may be readily selected for use in the SDA by one skilled in the art, such that the quencher dye sufficiently absorbs the fluorescence emitted by the donor dye. For example, the donor and quencher dyes are readily detected and differentiated by absorption at different wavelengths. Depending on the donor and quencher dyes, the quencher dye may act as a quencher in one instance and as a donor dye in other.

In this embodiment, the detector primer of SEQ ID NOs: 30-35 has a donor and quencher dye pair separated by a restriction enzyme recognition site located at the 5' end of the detector primer. Furthermore, the detector primer of SEQ ID NO: 30 has a sequence comprising a hairpin structure sequence located between the donor and quencher moities, where the restriction enzyme recognition site lies therein. The hairpin structure brings the two dyes in close proximity such that the fluorescence emitted by the donor dye is suppressed by the quencher dye. However, the detector primers of SEQ ID NOs: 31-35 have a linear sequence between the two dyes which is short enough in length for the quencher to absorb any fluorescence emitted by the fluorophore.

Many donor/quencher dye pairs known in the art are useful in embodiments of the present invention. These include, but are not limited to, fluorescein (FAM™; Glen Research; Sterling, Va.) /rhodamine (ROX™; Molecular Probes; Eugene, Oreg.); ROX™/P-(dimethyl aminophenylazo) benzoic acid (DABCYL™; Glen Research); FAM™/DABCYL™; fluorescein isothiocyanate (FITC)/tetramethylrhodamine isothiocyanate (TRITC); FITC/Texas Red™ (Molecular Probes); FITC/N-hydroxysuccinimidyl 1-pyrenebutyrate (PYB); FITC/eosin isothiocyanate (EITC); N-hydroxysuccinimidyl 1-pentanesulfonate (PYS)/

FITC; FITC/Rhodamine X; and FITC/tetramethylrhodamine (TAMRA). The selection of a particular donor/quencher pair is not critical.

However, for energy transfer quenching mechanisms, it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. ROX™ has an EMmax=608 nm and FAM™ has an EMmax of 520 nm. One skilled in the art would be knowledgeable in selecting the appropriate donor and quencher dye pair. P-(dimethyl aminophenylazo) benzoic acid (DABCYL™) is a non-fluorescent quencher dye which effectively quenches fluorescence from an adjacent fluorophore, e.g., FAM™ or 5-(2'-aminoethyl) aminonaphthalene (EDANS). Certain donor/quencher pairs are exemplified in this disclosure; however, others will be apparent to those skilled in the art and are also useful in the invention. Any dye pair which produces fluorescence quenching in the detector primers of the invention are suitable for use in the methods of the invention, regardless of the mechanism by which quenching occurs. Non-limiting examples of other quenchers include Black Hole Quencher™(Biosearch Technologies, Inc.; Novato, Calif.) and Iowa Black™ (Integrated DNA Technologies, Inc.; Corralville, Iowa).

Fluorescence is measured during the course of the nucleic acid amplification reaction to monitor the accumulation of specific amplification products. The fluorescent signal is proportional to the amount of specific amplicon produced. In the presence of HSV target nucleic acid sequence, fluorescence will increase. In the absence of target, fluorescence will remain consistently low throughout the reaction. An increase in fluorescence or a failure of fluorescence to change substantially indicates the presence or absence of HSV target sequence, respectively.

The fluorescence of the samples is typically measured over time to determine whether a sample contains HSV DNA. In one embodiment, fluorescence may be monitored for 60 passes over the course of one hour. Briefly, approximately every minute, data are collected regarding the amount of fluorescence measured in the sample container, a correction value (if necessary), and calibrators for each column. Data may be analyzed using the "MOTA" (Metric Other Than Acceleration) method of expressing results in terms of the area under a curve of a graph. The graph measures the number of passes (X-axis) versus relative fluorescent units (Y-axis) (see, FIG. 3). The greater the MOTA area, the more fluorescence generated and the more efficient the detection of amplified products.

Figure 4:
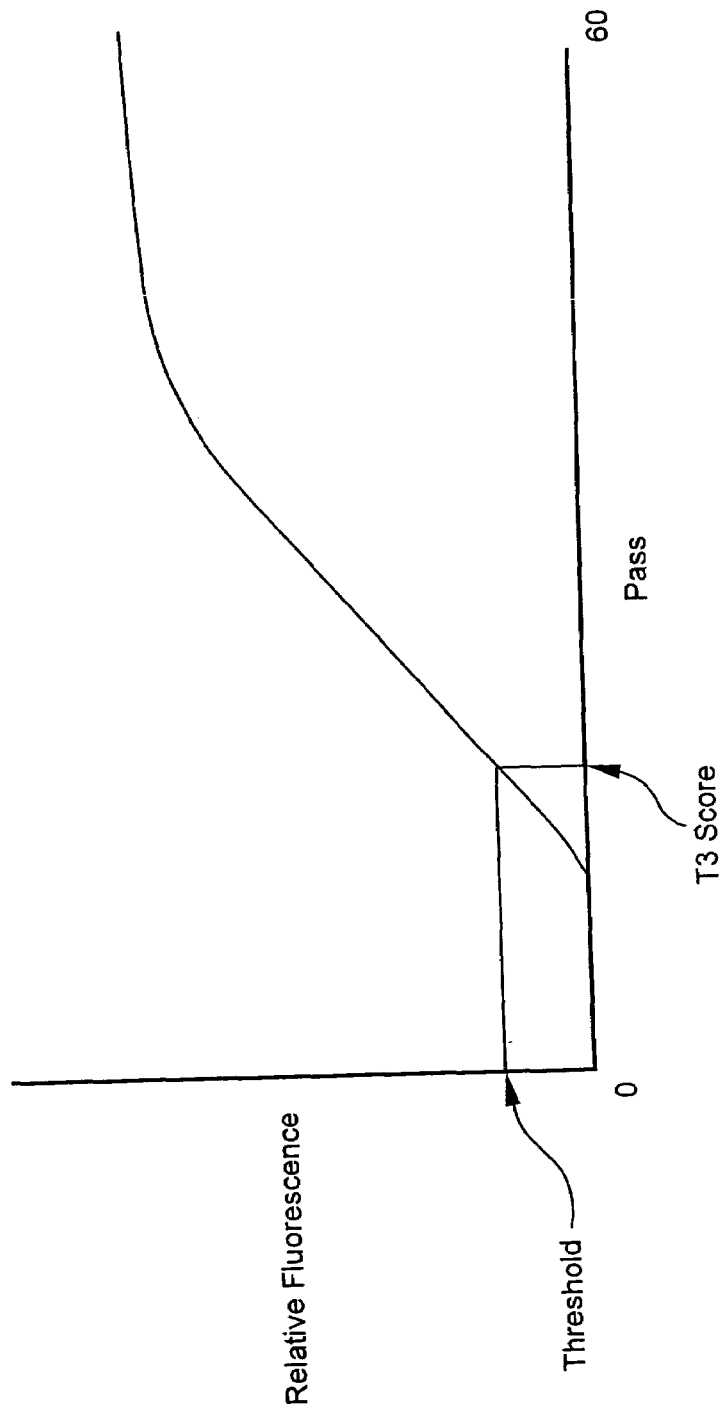
FIG. 4 is a graph showing the "PAT" algorithm used with the BD ProbeTec™ ET System.

Yet another embodiment uses a Passes After Threshold (PAT) algorithm, which is shown in FIG. 4, and is particularly developed for use with the BD ProbeTec™ ET System. Similar to MOTA, a higher PAT score indicates a more efficient SDA reaction. When using the PAT algorithm, the time at which the background corrected signal of fluorescence intensity crosses a predetermined threshold is designated as T3 ("Time-To-Threshold"). This graph also measures the number of passes to relative fluorescent units. The same T3 threshold value is used for every sample. The PAT score is equal to 60 minus the T3 value. Negative samples do not achieve the minimum threshold of fluorescence and are therefore assigned a PAT value of zero. Positive samples have PAT values greater than 0, preferably between 1 and 60, more preferably between 40-55, depending on the assay and target level. Lower T3 scores and corresponding higher PAT values correlate with a more efficient SDA. The PAT algorithm utilizes only the region of the amplification curve that is the most reproducible. As a result, the PAT algorithm method minimizes discernable differences between wells or samples, and is more precise than other methods of comparison between detectors. PAT can be performed automatically by the BD ProbeTec™ ET System. The BD ProbeTec™ ET printout provides a PAT score and a reportable result.

In yet a further embodiment, an "internal amplification control" ("IAC") may be incorporated into the present method to verify negative results and to identify potential inhibitory specimens or to facilitate quantification of organism load in a sample, such as but not limited to viruses, bacteria, and fungi. For diagnostic applications, simultaneous amplification and detection of two different DNA sequences, i.e., the HSV target sequence and the IAC target sequence, enable the use of an IAC. The "IAC target sequence" or "IAC sequence" is similar to the HSV target sequence with the exception that the IAC target sequences of SEQ ID NOs: 26-27 and of SEQ ID NOs: 48-49 are mismatched by about 5-10 bases compared to the HSV-1 and HSV-2 target sequences. These modified bases are sufficient to allow specific annealing of IAC adapter primers.

"IAC adapter primers" function similarly to the signal or adapter primers with the exception that the IAC adapter primers hybridize to an "IAC target sequence" or "IAC sequence" through an IAC target binding sequence. The IAC adapter primer also has a 5' tail portion containing a generic sequence which does not hybridize to the IAC target sequence. Rather a detector primer may hybridize to the tail portion of the IAC adapter primer complement. The IAC adapter primers used in the HSV-1 and HSV-2 SDA assays may be selected from SEQ ID NOs: 28-29 and 50-51, respectively, and are useful in the amplification of IAC target sequences. The IAC target binding sequence located at the 3' end of the IAC adapter primer differs from the HSV target sequence sufficiently such that the HSV-1 or HSV-2 adapter primers do not hybridize or interfere with the amplification of the IAC target sequence. In Tables 1 and 2, the IAC target binding sequence at the 3' end of the IAC adapter primer is indicated by lowercase underlining. The IAC adapter primers are useful in verifying negative results and in monitoring for specimens that inhibit the reaction. For quantitative SDA, competition for rate-limiting reagents between an IAC and a native target sequence may also be useful (Nadeau, et al., 1999 *Anal. Biochem.* 276: 177-187).

Detector primers of the invention may be used to detect either HSV target sequences or IAC target sequences. However, in one embodiment of the invention, detector primers used to detect the HSV-1 or HSV-2 target sequence are those of SEQ ID NOs: 30-33. The detector primers useful in detecting IAC target sequences are those selected from SEQ ID NOs: 34-35, where the donor and quencher dye pair is fluorescein (FAM™) and DABCYL™, respectively, and may be referred to herein as "IAC detector primers." One skilled in the art would be knowledgeable in selecting the appropriate detector primers having labels, such that the identification of the IAC target sequence is distinguishable from the identification of the HSV-1 or HSV-2 target sequence. Therefore, the detector primers used in the detection of HSV target sequence and IAC target sequence may be exchanged such that detector primers of SEQ ID NOs: 30-33 and may be used in the detection of IAC target sequences and SEQ ID NOs: 34-35 may be used in the detection of HSV target sequences.

Another embodiment of the invention relates to assaying multiple samples simultaneously in a high-throughput process. Samples include, but are not limited to those collected from cerebral spinal fluid (CSF), genital lesions, oral lesions, mucosal lesions, ocular specimens, dermal specimens, rectal swabs, vaginal swabs, vaginal secretions, urine, peripheral blood leukocytes, and tissue (such as from a brain biopsy). The samples may be assayed in plates, slides, wells, dishes, beads, particles, cups, strands, chips, and strips. In one embodiment, the methods are performed in 96 microwell plates in a format consistent with that used in the BD ProbeTec™ ET CT/GC Amplified DNA Assay. The method is performed in a dried micro-well format, where the dried composition comprises all of the primers and probes necessary for carrying out SDA detection of HSV-1 or HSV-2 for use in simultaneously assaying multiple samples.

Assays detecting the presence of a selected target sequence according to the methods of the invention may be performed in solution or on a solid phase. Real-time or endpoint homogeneous assays in which the detector nucleic acid functions as a primer are typically performed in solution. Hybridization assays using the detector primers of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

The primers and probes used for detecting and identifying HSV-1 target sequence are listed in Table 1. The specific HSV target binding sequences are underlined and capitalized, while the restriction enzyme endonuclease sites are indictated in lower case italics. For the IAC adapter primers, the IAC target binding sequence is indicated by lower case underlining. All primers are listed in the 5'→3' direction.

TABLE 1

| PRIMER | SEQUENCES FOR AMPLIFICATION AND DETECTION OF HERPES SIMPLEX VIRUS 1 DNA | SEQ ID NO: |
|---|---|---|
| | PCR AMPLIFICATION PRIMERS FOR THE HSV-1 TARGET SEQUENCE | |
| PCRL1.0 | GCGGAATTCGACCCTTGGTTCC | 5 |
| PCRR1.0 | GCGGGATCCCCAACCACCACAC | 6 |
| | LEFT (FIRST) AMPLIFICATION PRIMER | |
| HSV1GGLP1.0 | ACCGCATCGAATGACTGT*ctcggg*CTGTTCTCGTTCCTC | 7 |
| HSV1GGLP1.1 | ACCGCATCGAATGACTGT*ctcggg*CTGTTCTCGTTCCT | 8 |
| | RIGHT (SECOND) AMPLIFICATION PRIMER | |
| HSV1GGRP1.0 | CGATTCCGCTCCAGACTT*ctcggg*CACCAATACACAAAAA | 9 |
| HSV1GGRP1.1 | CGATTCCGCTCCAGACTT*ctcggg*CAACAATACACACAAA | 10 |
| HSV1GGRP2.0 | CGATTCCGCTCCAGACTT*ctcggg*CACCAATACACAAAAAC | 11 |
| HSV1GGRP2.1 | CGATTCCGCTCCAGACTT*ctcggg*CAACAATACACACAAAC | 12 |
| HSV1GGRP3.0 | CGATTCCGCTCCAGACTT*ctcggg*CACCAATACACAAAAACG | 13 |
| HSV1GGRP3.1 | CGATTCCGCTCCAGACTT*ctcggg*CAACAATACACACAAACG | 14 |
| HSV1GGRP4.0 | CGATTCCGCTCCAGACTT*ctcggg*CAATACACAAAAACGAT | 15 |
| HSV1GGRP4.1 | CGATTCCGCTCCAGACTT*ctcggg*CAATACACACAAACGAT | 16 |
| HSV1GGRP4.2 | CGATTCCGCTCCAGACTT*ctcggg*CAATACACACAAATGAT | 17 |
| HSV1GGRP5.2 | CGATTCCGCTCCAGACTT*ctcggg*AAGGTGTGGATGAC | 18 |
| | ADAPTER PRIMER | |
| HSV1GGAD1.0 | ACGTTAGCCACCATACGGATCCGTCATCCACACCTTATC | 19 |
| HSV1GGAD2.1 | ACGTTAGCCACCATACGGATGGACACCCTCTTCGTCGTC | 20 |
| HSV1GGAD3.0 | ACGTTAGCCACCATACTTGAGGACACCCTCTTCGTCGTC | 21 |
| HSV1GGAD3.1 | ACGTTAGCCACCATACTTGAGGACACCCTCTTCGTCG | 22 |
| | LEFT (FIRST) BUMPER PRIMER | |
| HSV1GGLB1.0 | GACGCCTCAACATAC | 23 |
| | RIGHT (SECOND) BUMPER PRIMER | |
| HSV1GGRB1.0 | GTGTGTCGCCATCG | 24 |
| HSV1GGRB1.1 | AGGTGTGTCGCCAT | 25 |

TABLE 1-continued

PRIMER SEQUENCES FOR AMPLIFICATION AND DETECTION OF HERPES SIMPLEX VIRUS 1 DNA

| | | SEQ ID NO: |
|---|---|---|
| IAC TARGET SEQUENCE | | |
| HSV1IAC8.1 | CTGTTCTCGTTCCTCACTGCCTCCCCCGCCCTGGACACCCTC TTGCTGCTGAGCACCGTCATCCACACCTT | 26 |
| HSV1IAC8.7 | CTGTTCTCGTTCCTCACTGCCTCCCCCGCCCTGGACACCCTC TGTTCATCTAGCACCGTCATCCACACCTT | 27 |
| IAC ADAPTER PRIMER | | |
| HSV1 IACAD8.1 | ACTGATCCGCACTAACGACTggacaccctcttgctgctg | 28 |
| HSV1 IACAD8.7 | ACTGATCCGCACTAACGACTggacaccctctgttcatct | 29 |
| DETECTOR PRIMER | | |
| TBD10.2 D/R | (DABCYL)-TAGCGcccgagCGCT-(ROX)- ACGTTAGCCACCATACGGAT | 30 |
| TBD15 D/R | (DABCYL)-TGcccgagT-(ROX)-ACGTTAGCCACCATACGGAT | 31 |
| TBD16 (D/R) | (DABCYL)-TcccgagT-(ROX)-ACGTTAGCCACCATACGGAT | 32 |
| MPC.DR | (DABCYL)-TCcccgagT-(ROX)-ACGTTAGCCACCATACTTGA | 33 |
| MPC2.FD | (FAM)-TCcccgagT-(DABCYL)-ACTGATCCGCACTAACGACT | 34 |
| AltD8 (F/D) | (FAM)-AcccgagT-(DABCYL)-AGCTATCCGCCATAAGCCAT | 35 |

The primers and probes used for detecting and identifying HSV-2 target sequence are listed in Table 2.

TABLE 2

PRIMER SEQUENCES FOR AMPLIFICATION AND DETECTION OF HERPES SIMPLEX VIRUS 2 DNA

| | | SEQ ID NO: |
|---|---|---|
| PCR AMPLIFICATION PRIMERS FOR THE HSV-2 TARGET SEQUENCE | | |
| HSV2PCRL | GCGGAATTCATTCTTGGGCCGCT | 36 |
| HSV2PCRR | GCGGGATCCACGTAACGCACGCT | 37 |
| LEFT (FIRST) AMPLIFICATION PRIMER | | |
| HSV2GGLP1.0 | ACCGCATCGAATGACTGTctcgggCTGTTCTGGTTCCTA | 38 |
| RIGHT (SECOND) AMPLIFICATION PRIMER | | |
| HSV2GGRP1.0 | CGATTCCGCTCCAGACTTctcgggCGACCAGACAAACGAA | 39 |
| HSV2GGRP1.1 | CGATTCCGCTCCAGACTTctcgggACCAGACAAACGAAC | 40 |
| HSV2GGRP1.2 | CGATTCCGCTCCAGACTTctcgggCGACCAGACAAACGAAC | 41 |
| HSV2GGRP2.0 | CGATTCCGCTCCAGACTTctcgggAACGCCGCCGTGT | 42 |
| HSV2GGRP5.2 | CGATTCCGCTCCAGACTTctcgggCCGTGTGGATGGT | 43 |
| ADAPTER PRIMER | | |
| HSV2GGAD1.0 | ACGTTAGCCACCATACGGATCCACCATCCACACGGCGGC | 44 |
| HSV2GGAD2.0 | ACGTTAGCCACCATACTTGATGCTCTAGATATCCTCTTTATCAT | 45 |
| LEFT (FIRST) BUMPER PRIMER | | |
| HSV2GGLB1.0 | CACACCCCAACACAT | 46 |
| RIGHT (SECOND) BUMPER PRIMER | | |
| HSV2GGRB1.0 | TTGTGCTGCCAAGG | 47 |

TABLE 2-continued

PRIMER SEQUENCES FOR AMPLIFICATION AND DETECTION OF HERPES SIMPLEX VIRUS 2 DNA

| | | SEQ ID NO: |
|---|---|---|
| IAC TARGET SEQUENCE | | |
| HSV2-IAC 5.2A1 | CTGTTCTGGTTCCTAACGGCCTCCCCTGCTCTAGATATCCTCT TTACTACCAGCACCACCATCCACACGG | 48 |
| HSV2-IAC 5.2A2 | CTGTTCTGGTTCCTAACGGCCTCCCCTGCTCTAGATATCCTCT TAACTACCAGCACCACCATCCACACGG | 49 |
| IAC ADAPTER PRIMER | | |
| HSV2GG IAC ADA1.0 | ACTGATCCGCACTAACGATtgctctagatatcctctttactac | 50 |
| HSV2GGIAC ADA2.0 | ACTGATCCGCACTAACGACTtgctctagatatcctcttaactac | 51 |
| DETECTOR PRIMER | | |
| TBD10.2 D/R | (DABCYL)-TAGCGcccgagCGCT-(ROX)- ACGTTAGCCACCATAC GGAT | 30 |
| TBD15 D/R | (DABCYL)-TGcccgagT-(ROX)-ACGTTAGCCACCATACGGAT | 31 |
| TBD16 (D/R) | (DABCYL)-TcccgagT-(ROX)-ACGTTAGCCACCATACGGAT | 32 |
| MPC.DR | (DABCYL)-TCcccgagT-(ROX)-ACGTTAGCCACCATACTTGA | 33 |
| MPC2.FD | (FAM)-TCcccgagT-(DABCYL)-ACTGATCCGCACTAACGACT | 34 |
| ALTD8 (F/D) | (FAM)-AcccgagT-(DABCYL)-AGCTATCCGCCATAAGCCAT | 35 |

The nucleic acid primers of the present invention are designed based on a consensus sequence generated by analyzing the Glycoprotein G (US4) sequence region of the HSV gene for various strains. (See, FIGS. 1 and 6; Tables 1 and 2). Also shown are bumper primers, adapter primers, and detector primers for use in the SDA and universal detection methods. The designed HSV-1 primers specifically amplify an HSV-1 target sequence that is recognized in all strains as exemplified in Table 4. The HSV-2 primers are designed to specifically amplify an HSV-2 target sequence that is recognized in all strains as exemplified in Table 7. Since the homology between the HSV-1 and HSV-2 target sequences is about 90%, the primers are carefully designed to specifically distinguish between HSV-1 and HSV-2. Also contemplated in the invention, are sequences that substantially homologous to the target binding sequences and primers containing such substantially homologous target binding sequences listed in Tables 1 and 2.

In one embodiment of the present invention, an HSV-1 target region is first selected from the complete HSV-1 genomic sequence of Human HSV-1, strain 17 (NCBI accession no. X14112) having 152,261 bases in length. The glycoprotein "US4" gene is located at 136,744-137,460 bases. The HSV-1 Left bumper primer (HSV1LB1.0) (5' end) is located at nucleic acid 137,256. The HSV-1 Right bumper primer (HSV1RB1.1) (5' end) is located at nucleic acid 137,382. Primers for all HSV-1 SDA systems are located within these bumper primer coordinates.

Another embodiment of the invention relates to the complete HSV-2 genome sequence of Human HSV-2, strain HG52 (NCBI accession no. Z86099) having 154,746 bases in length. The glycoprotein "US4" gene is located at 137,878-139,977 bases. The HSV-2 Left bumper primer (HSV2LB1.0) (5' end) is located at position 139,773. The HSV-2 Right bumper primer (HSV2RB1.0) (5' end) is located at position 139896. Primers for all IHSV-2 SDA systems are located within the bumper primer coordinates.

PCR amplification primers are designed for cloning the HSV target DNA into a plasmid vector. The HSV-1 and HSV-2 PCR amplification primers of SEQ ID NOs: 5-6 and SEQ ID NOs: 36-37, respectively, are complementary to highly conserved target sequence regions of the HSV genome. The PCR amplification primers amplify an HSV target sequence region comprising a DNA fragment of the Glycoprotein G (US4) gene of HSV. The amplified fragment of the herpes simplex virus (HSV) genome containing the HSV target region is directionally cloned into a plasmid vector containing convenient restriction enzyme sites. Although the HSV fragment may be cloned into any plasmid vector as is understood by the skilled artisan, in one embodiment of the invention, the amplified HSV-1 and HSV-2 fragments are cloned into the *Escherichia coli* plasmid vectors, pUC19 (Genbank/EMBL Accession No. L09137) and pUC18 (Genbank/EMBL Accession No. L09136), respectively, using PCR amplification primers specific to the selected HSV target regions. The HSV fragment is referred to as the HSV target stock. The target HSV DNA may be quantified using the PicoGreen® double stranded DNA Quantitation Assay (Molecular Probes, Inc.). The presence of "L" or "R" in the primer name listed in Tables 1 and 2 indicates "left" or "right" primers, respectively, when used in amplification reactions.

In one embodiment of the invention, PCR amplification primers SEQ ID NOs: 5-6 and 36-37 initially amplify a 152 and 254 base pair fragment of the Glycoprotein G gene of the HSV-1 and HSV-2 gene, respectively. The HSV-1 and HSV-2 Left PCR primer of SEQ ID NOs: 5 and 36, respectively, are each designed with an EcoRI restriction enzyme site. The HSV-1 and HSV-2 Right PCR primer of SEQ ID NOs: 6 and 37, respectively, each have a BamHI restriction enzyme site. This fragment is then positionally cloned into the pUC plasmid vector. The exemplified plasmid vector is pUC19 and pUC18 for HSV-1 and HSV-2, respectively, which have restriction enzyme sites EcoRI and BamHI. After purification and linearization by restriction enzyme digestion, the HSV target fragment is then exponentially amplified using HSV amplification primers and bumper primers.

The target binding sequences and primers of the invention are useful in nucleic acid amplification. In one embodiment, the primers are particularly useful in strand displacement amplification (SDA). This is an isothermal method of nucleic acid amplification in which extension of primers, nicking of hemimodified restriction endonuclease recognition/cleavage site, displacement of single-stranded extension products, annealing of primers to the extension products (or the original target sequence) and subsequent extension of the primers occur concurrently in a reaction mixture. Furthermore, SDA allows for target sequence replication in excess of $10^{10}$ fold in less than 15 minutes. Whereas, in PCR, the steps of the reaction occur in separate phases or cycles as a result of temperature cycling in the reaction. Thermophilic Strand Displacement Amplification (tSDA) is performed essentially as the conventional SDA method described herein and by Walker, et al. (1992, *Proc. Natl. Acad. Sci USA*. USA 89:392-396 and 1992, *Nucl. Acids Res.* 20:1691-1696) with substitution of the thermostable polymerase and thermostable restriction endonuclease. The temperatures may be adjusted to the higher temperature appropriate for the substituted enzymes.

An alternative method of detecting HSV amplification products or amplified target sequence may be by detecting a characteristic size by polyacrylamide or agarose gel electrophoresis, where the agarose is stained with ethidium bromide. The amplified products generated using the HSV-1 or HSV-2 amplification primers may also be detected by quantitative hybridization, or equivalent techniques for nucleic acid detection known to one skilled in the art of molecular biology (Sambrook et al, *Molecular Cloning: A Laboratory Manual*, Cold Spring Harbor Laboratory, Cold Spring, N.Y. (1989)).

The primers listed in Tables 1 and 2 are useful in the detection and identification of HSV-1 and HSV-2 in a sample. As used herein, the S1 and S2 amplification primers represent the first and second amplification primers, respectively; while the B1 and B2 bumper primers represent the first and second bumper primers, respectively. Briefly, in the SDA method, the S1 amplification primer hybridizes to a single-stranded HSV target sequence. Just upstream or 5' of the S1 amplification primer, a first bumper primer, B1, hybridizes to the single-stranded HSV target sequence. DNA polymerase extends the 3' ends of the B1 bumper primer and the S1 amplification primer, where the extension of the B1 bumper primer eventually displaces the S1 SDA extension product. The S1 SDA extension product is captured by the S2 amplification primer and B2 bumper primer which anneals upstream of the S2 amplification primer. DNA polymerase extends the 3' ends of the S2 SDA and B2 bumper primers, where the extension of the B2 bumper primer displaces the downstream S2 SDA extension product. The S1 amplification primer anneals to the displaced S2 amplification primer extension product and DNA polymerase extends the 3' end of the hybridized S1 amplification primer, producing a double-stranded molecule having the S2 amplification primer extension product and its complement strand. Each strand has a nickable restriction enzyme recognition site at either end. Upon addition of the corresponding restriction enzyme, the modified DNA strand, containing a thiolated cytosine, is nicked forming a short nicked tail and a long extension product 3' of the nick site. DNA polymerase extends the short nicked tail from the 3' end of the short nicked tail in a 5'→3' direction displacing the single-stranded long extension product. Briefly, the nicked tail of the S2 amplification primer extension product and the nicked tail of its complement displace the single-stranded nicked S2 amplification primer extension product and single-stranded nicked complement S2 amplification primer extension product, respectively. In one embodiment, BsoBI enzyme is used to nick and cleave or cut each strand having a sequence of SEQ ID NOs: 52-53 and 54-55, respectively. The nick sites, indicated below, are incorporated into the amplification primer sequence and require a hemi-phosphorothiolated recognition sequence (dCsTP, thiolated cytosine). Although a nick site, SEQ ID NO: 53 is prone to double-stranded cleavage even in the presence of dCsTP and is not a preferred sequence in designing nickable amplification primers.

```
Nick Sites:
5'-CTCGGG-3'          (SEQ ID NO: 52)
and

5'-CCCGGG-3'          (SEQ ID NO: 53)

Cut Sites:
5'-CTCGAG-3'          (SEQ ID NO: 54)
and

5'-CCCGAG-3'          (SEQ ID NO: 55)
```

In a further embodiment of the invention, a detector probe is useful in detecting the HSV target sequence. The S1 amplification primer and a detector primer specific for the HSV target sequence may be used, where the detector primer has a an HSV target binding sequence. DNA polymerase extends from the 3' ends of the S1 primer and the detector primer. Extension of the S1 primer displaces the downstream detector primer extension product into solution, where it is captured and hybridizes to a complementary S2 amplification primer. DNA polymerase extends the 3' end of the S2 amplification primer and opens up the secondary structure of the detector primer forming a double-stranded restriction enzyme site and separating the two dyes (fluorophore and quencher pair) to such a distance as to disable the quenching ability of the quencher and to generate fluorescence. Additional fluorescence is produced by cleaving the restriction enzyme recognition site and further separating the fluorophore and quencher.

Enzymes useful in the SDA method are those that create a single-stranded nick in a hemi-phosphorothioated recognition sequence, where the incorporation of phosphorothioated nucleotides does not prevent further rounds of nicking and repair. Non-limiting examples of enzymes that possess these characteristics include: HincII, BsoBI, AvaI, NciI, and Fnu4HI. Useful DNA polymerases are those that initiate DNA synthesis at the single-stranded nick site, incorporate phosphorothioated nucleotides into the extending nucleic acid chain, and displace strands without 5'→3' exonuclease activity. Cleavage refers to the breaking of the phosphodiester bond of the double-stranded or single-stranded DNA. Non-limiting examples of DNA polymerases that exhibit those characteristics include: exonuclease-deficient Klenow and exonuclease-deficient fragments of Bst polyermase and Bca polymerase. Although other DNA polymerases and restriction enzymes are suitable for SDA (Walker et al. *Proc.*

Natl. Acad. Sci USA, Vol. 89, pp. 392-396, January 1992, Applied Biological Sciences), exo-Bst polymerase and BsoBI were chosen for their thermal characteristics and compatibility with one another. In one embodiment of the invention, BsoBI restriction endonuclease recognition sites are used and designated in italics (see, Tables 1 and 2). It will be readily apparent that the HSV target binding sequences may be used alone to amplify the HSV target in reactions which do not require specialized sequences or structures (e.g., PCR) and that other specialized sequences required by amplification reactions other than SDA (e.g., an RNA polymerase promoter) may be substituted in the system, for example for the RERS-containing sequence described herein.

The target stock may then be amplified in the presence of amplification primers, alone or in combination with bumper primers, signal/adapter primers for universal detection, and a universal detector primer. For an amplification reaction, at least one pair comprising one "left" amplification primer is selected and one "right" amplification primer is selected to amplify each strand of the HSV target stock sequence. In addition to the left and right amplification primers, in the SDA reaction, one left and right bumper primer pair is initially used. Furthermore, for detection, a signal/adapter primer and a detection primer is selected and used to detect and identify the HSV target sequence.

Several HSV systems that specifically amplify and detect either HSV-1 or HSV-2 DNA are embodied in the present invention. For example, HSV-1 systems may include the following primers: HSV1GGLP1.1, HSV1GGRP5.2, HSV1GGAD2.1, HSV1GGLB1.0, HSV1GGRB1.1, and TBD16 (D/R) or alternatively, HSV1GGLP1.1, HSV1GGRP5.2, HSV1GGAD3.0 or HSV1GGAD3.1, HSV1GGLB1.0, HSV1GGRB1.1, MPC.DR, HSV1IAC AD8.1 or HSV1IACAD8.7, MPC2.FD. In another embodiment, HSV-2 systems using various combinations of primers are listed in Table 3. Other combinations of primers are contemplated however, one skilled in the art would be knowledgeable in combining the primers in order to detect HSV-1 or HSV-2 in a sample. The primers may be selected from those listed in Tables 1 and 2, and tested in statistically designed experiments in order to identify HSV-1 or HSV-2 in a sample. Alternatively, primers that are specific fro HSV-1 or HSV-2 and substantially homologous to those listed in Tables 1 and 2 may also be used in the detection of HSV-1 or HSV-2 target sequences.

TABLE 3

HSV-2 SDA SYSTEM DESIGNS

| HSV2 SDA SYSTEM | PRIMERS USED IN SYSTEM | |
| --- | --- | --- |
| HSV2GG 1.0 | HSV2GGRP1.0 | Right amplification primer |
| | HSV2GGLP1.0 | Left amplification primer |
| | HSV2GGRB1.0 | Right Bumper primer |
| | HSV2GGLB1.0 | Left Bumper primer |
| | HSV2GGAD1.0 | Adapter primer |
| HSV2GG 1.1 | HSV2GGRP1.1 | Right amplification primer |
| | HSV2GGLP1.0 | Left amplification primer |
| | HSV2GGRB1.0 | Right Bumper primer |
| | HSV2GGLB1.0 | Left Bumper primer |
| | HSV2GGAD1.0 | Adapter primer |
| HSV2GG 1.2 | HSV2GGRP1.2 | Right amplification primer |
| | HSV2GGLP1.0 | Left amplification primer |
| | HSV2GGRB1.0 | Right Bumper primer |
| | HSV2GGLB1.0 | Left Bumper primer |
| | HSV2GGAD1.0 | Adapter primer |

TABLE 3-continued

HSV-2 SDA SYSTEM DESIGNS

| HSV2 SDA SYSTEM | PRIMERS USED IN SYSTEM | |
| --- | --- | --- |
| HSV2GG 2.0 | HSV2GGRP2.0 | Right amplification primer |
| | HSV2GGLP1.0 | Left amplification primer |
| | HSV2GGRB1.0 | Right Bumper primer |
| | HSV2GGLB1.0 | Left Bumper primer |
| | HSV2GGAD2.0 | Adapter primer |
| HSV2GG 5.2 | HSV2GGRP5.2 | Right amplification primer |
| | HSV2GGLP1.0 | Left amplification primer |
| | HSV2GGRB1.0 | Right Bumper primer |
| | HSV2GGLB1.0 | Left Bumper primer |
| | HSV2GGAD2.0 | Adapter primer |

For commercial convenience, amplification primers for specific detection and identification of nucleic acids may be packaged in the form of a kit. Generally, such a kit contains at least one pair of HSV amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., a primer tagged with a label suitable for use as an assay probe, and/or reagents or means for detecting the label.

In one embodiment of the invention, a kit is provided that comprises a first amplification primer or S1 SDA amplification primer, and a second amplification primer or S2 SDA amplification primer. The kit may further comprise a first B1 bumper primer and second B2 bumper primer; an adapter primer; a detector primer; and optionally, reagents for simultaneously detecting an Internal Amplification Control (IAC) target sequence, including IAC adapter primers and an IAC target sequence. The kit may comprise of primers specifically for HSV1 or HSV-2, or the kit may comprise of primers directed to both HSV-1 and HSV-2, where one skilled in the art would understand that amplification reactions to detect and identify HSV-1 utilize the HSV-1 primers, and to detect and identify HSV-2 utilize HSV-2 primers. In order to identify whether a sample contains HSV-1 or HSV-2 DNA, primers for HSV-1 and HSV-2 should not be mixed.

In yet another embodiment, the kit and primers of the invention may be used to detect and diagnose whether a clinical sample contains HSV-1 or HSV-2 DNA. The clinical sample may be amplified and detected using the SDA amplification primers, or may be used in an SDA reaction further comprising bumper primers, adapter primers, and detector primers. In an embodiment of the invention, IAC adapter primers may be used as an internal amplification control for the reactions, in addition to positive and negative controls for HSV-1 or HSV-2. One skilled in the art would understand, from reading the description herewith and from the general methods and techniques in the art, how to make and use the primers for the detection and identification of HSV-1 and HSV-2 in a sample.

Furthermore, in a commercial embodiment, a composition comprising the primers of the invention and reagents for SDA may be provided in a dried or liquid format. The composition is more stable and easily manipulated when in a dried format. The dried composition may be added or pre-treated to a solid phase such as a microtiter plate, microarray, or other appropriate receptacle, where the sample and SDA buffer need only be added. This format facilitates assaying multiple samples simultaneously and is useful in high-throughput methods. In an embodiment of the invention, the BD ProbeTec™ ET instrument may be used.

It is to be understood that a nucleic acid according to the present invention which consists of a target binding sequence and, optionally, either a sequence required for a selected amplification reaction or a sequence required for a selected detection reaction may also include certain other sequences which serve as spacers, linkers, sequences for labeling or binding of an enzyme, or other uses. Such additional sequences are typically known to be necessary to obtain optimum function of the nucleic acid in the selected reaction.

The contents of all patents, patent applications, published PCT applications and articles, books, references, reference manuals and abstracts cited herein are hereby incorporated by reference in their entirety to more fully describe the state of the art to which the invention pertains.

As various changes may be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

EXAMPLES

The Examples herein are meant to exemplify the various aspects of carrying out the invention and are not intended to limit the scope of the invention in any way. The Examples do not include detailed descriptions for conventional methods employed, such as in the construction of vectors or the insertion of cDNA into such vectors. Such methods are well known to those skilled in the art and are described in numerous publications, for example, J. Sambrook and D. W. Russell, *Molecular Cloning: a Laboratory Manual*, $3^{rd}$ Edition, Cold Spring Harbor Laboratory Press, USA, (2001).

Example 1

Cloning of HSV-1 Glycoprotein-G Strand Displacement Amplification Target Region

PCR was performed on DNA from the HSV-1 (strain ATCC: VR-539) using the PCR amplification primers of SEQ ID NO: 5 and SEQ ID NO: 6 identified in Table 1. These primers were designed to amplify a 152 base pair fragment within the Glycoprotein G (US4) gene of HSV-1. PCR amplified DNA was inserted into a pUC19 plasmid vector (Gibco BRL; Grand Island, N.Y.). The recombinant clone was named HSVIGG Plasmid #1. Plasmid #1 DNA was purified and linearized by digestion with BamH1 restriction enzyme. The DNA was then purified using QIAquick (Qiagen, Inc.; Valencia, Calif.) spin columns and quantified by analysis with fluorescent Picogreen® reagent. Dilutions of the target HSV-1 DNA for future experiments were prepared in water containing 10 ng/μl human DNA. Specific HSV-1 strain dilutions and the results of HSV-1 detection in each dilution are shown in FIG. 5. A "plus" symbol indicates the presence of HSV-1 in the sample; a "minus" symbol indicates the absence of HSV-1 in the sample; and a question mark indicates the suspected contamination of the sample. All strains were positive at 1:10 dilution of Stock, except sample O-2526. At a 1:1,000 dilution of the stock, 20 of the 23 strains were positive. At a 1:100,000 dilution of the stock, 15 of 23 strains were positive.

Example 2

Amplification of Cloned HSV-1 DNA

As an initial step in the assay for detecting HSV-1 DNA, an SDA system for amplification of HSV-1 DNA was developed using the target nucleic acid method described in Example 1. The analytical senstivity of the DNA amplification assay was estimated using dilutions of the cloned plasmid. Eight replicate SDA reactions were performed at each target level. These eight reactions were equivalent to 100, 50, 25, 12.5, 6.25 and 0 copies of double stranded DNA per reaction. Amplification was conducted at 52° C. using a BD ProbeTec™ ET instrument (BD Diagnostic Systems; Sparks, Md.) with 50 nM each of HSV1GGLB1.0 and HSV1GGRB1.0 bumper primers, 100 nM of HSV1GGLP1.0 left amplification primer, 500 nM HSV1GGRP1.0 right amplification primer, 250 nM HSV1GGAD1.0 adapter primer, 500 nM TBD10.2 D/R detector primer. The sequences of these primers are listed in Table 1. Final buffer conditions were as follows: 143 mM Bicine, 82 mM KOH, 25MM $KiPO_4$, 12.5% DMSO, 5 mM magnesium acetate, 500 mM 2'-deoxycytosine-5-o-(1-thiotriphosphate)($dC_sTP$), 100 nM each of dATP, dGTP, and dTTP, 100 ng/μl BSA, approximately 12 units of Bst polymerase and approximately 30 units of BsoBI restriction endonuclease.

Fluorescence was monitored for 60 passes over the course of one hour. Results were expressed in terms of area under the curve or "MOTA" score. Positive MOTA scores can be readily determined by routine experimentation. For the purpose of the present invention, MOTA scores greater than or equal to 3500 were considered "positive." The lowest level of HSV 1 GG target DNA at which the assay yielded 100% positive results was 100 copies per reaction. Seven of eight replicates (87.5%) were also positive at fifty copies of target DNA per reaction.

Example 3

Detection of Herpes Simplex 1 Virus Particles by SDA

To verify the ability of the primers and probes of the invention to detect HSV-1, SDA was performed on four strains of HSV-1 obtained from American Type Culture Collection (ATCC; Manassas, Va.), 10 strains obtained from Quest Diagnostic (Baltimore, Md.) and fourteen untyped HSV samples from Ohio State University (OSU).

The untyped strains of HSV were characterized by amplifying a region of the DNA polymerase gene by PCR. One set of amplification primers was designed to amplify the same region in both HSV-1 and HSV-2. The two types of virus were distinguishable by the presence of an ApaI restriction endonuclease recognition site in the HSV-2 PCR fragment that is not present in PCR products generated from strains of HSV-1. When incubated with the ApaI restriction enzyme, the HSV-2-derived amplification products are cleaved into two shorter fragments while those obtained from HSV-1 remain intact. Restricted fragments were resolved on agarose gel electrophoresis with appropriate controls.

The concentrations of the viral stocks used to evaluate the presence or absence of HSV in an SDA system were not known. The viral stocks were diluted 1:10 in phosphate buffered saline and 10 μL of this suspension was tested by SDA. Results are shown in Table 4. All strains of HSV-1 were detected using the HSV-1 amplification primers demonstrating the ability of disclosed primers and probes to detect strains of HSV-1 from a diversity of sources. Of the previously untyped 14 strains of HSV typed by ApaI restriction digest, nine were determined to be HSV-1, four were determined to be HSV-2 and one did not amplify by PCR (see, Tables 4 and 5).

Example 5

Specificity of SDA for HSV-1 DNA

Sixteen strains of HSV-2 were tested with the HSV1GG SDA system. Ten microliters of each suspension of HSV-2 dilution were added per reaction. One of the 17 stocks tested positive with the HSV1GG system. The results are shown in Table 5. In addition, 23 other microorganisms were tested using the primers and probes of the disclosed inventive method. These microorganisms included bacteria, yeast and other viruses likely to be encountered in clinical specimens. None of the organisms tested positive for HSV-1. Results are shown in Table 6.

TABLE 4

STRAINS OF HERPES SIMPLEX 1 VIRUS TESTED BY SDA

| HSV TYPE | SAMPLE # | COMMENTS | APA1 GEL RESULTS | HSV-1GG (MOTA) | HSV-1GG (PAT) |
|---|---|---|---|---|---|
| HSV-1 | OSU 0-2021 | previously untyped | HSV-1 | 16970 | 45.91 |
| HSV-1 | OSU 0-450 | previously untyped | HSV-1 | 105400 | 50.07 |
| HSV-1 | OSU 0-1010 | previously untyped | HSV-1 | 156280 | 52.43 |
| HSV-1 | OSU 0-2526 | previously untyped | HSV-1 | 154715 | 51.96 |
| HSV-1 | OSU D-8-1973 | previously untyped | HSV-1 | 149720 | 54.73 |
| HSV-1 | OSU 7-370 | previously untyped | HSV-1 | 152600 | 54.56 |
| HSV-1 | OSU 0116-3 | previously untyped | HSV-1 | 175610 | 54.77 |
| HSV-1 | OSU 1136 | previously untyped | HSV-1 | 165410 | 53.36 |
| HSV-1 | OSU A.P. | previously untyped | HSV-1 | 225340 | 54.62 |
| HSV-1 | ATCC 260 VR | ATCC | HSV-1 | 148960 | 54.78 |
| HSV-1 | ATCC VR-733 | ATCC | HSV-1 | 248080 | 54.73 |
| HSV-1 | ATCC VR-735 | ATCC | HSV-1 | 153760 | 54.46 |
| HSV-1 | ATCC VR-539 | ATCC | HSV-1 | 173860 | 54.47 |
| HSV-1 | Clin1 | Quest Diagnostics | HSV-1 | 250570 | 54.33 |
| HSV-1 | Clin2 | Quest Diagnostics | HSV-1 | 222590 | 54.52 |
| HSV-1 | Clin3 | Quest Diagnostics | HSV-1 | 126780 | 51.51 |
| HSV-1 | Clin4 | Quest Diagnostics | HSV-1 | 262540 | 54.63 |
| HSV-1 | Clin5 | Quest Diagnostics | HSV-1 | 180530 | 54.44 |
| HSV-1 | Clin6 | Quest Diagnostics | HSV-1 | 12750 | 35.12 |
| HSV-1 | Clin7 | Quest Diagnostics | HSV-1 | 115500 | 50.31 |
| HSV-1 | Clin8 | Quest Diagnostics | HSV-1 | 184130 | 54.29 |
| HSV-1 | Clin9 | Quest Diagnostics | HSV-1 | 197860 | 52.98 |
| HSV-1 | Clin10 | Quest Diagnostics | HSV-1 | 160660 | 50.99 |

Example 4

Analytical Sensitivity of the SDA Method

To determine the limit of detection of the HSV-1 assay using the primers and probes disclosed in the present invention, SDA reactions were performed on dilutions of cloned target nucleic acid and serial dilutions of viral particles. The stock of viral particles was enumerated by electron microscopy (Electron Microscopy Bioservices). Sixteen replicates were tested at each target level.

To verify the sensitivity and specificity of the assay, 23 stains of HSV-1 from various geographical locations were tested at a 1:10, 1:1,000 and 1:100,000 dilution of the organism stock. The titer of the samples from the previously un-typed strains and from Quest Diagnostics was unknown. The titer of the two stocks of HSV-1 from ATCC were approximately as follows: VR260, $1.5 \times 10^4$ TCID/μL and VR-539, $2.0 \times 10^5$ TCID/μl. Results are shown in FIG. 5. All strains were positive at 1:10 dilution of the stock suspension, except Strain #0-2526. Of the 23 strains, 20 tested positive at 1:1000 dilution of the stock, and 15 strains tested positive at dilution of 1:100,000.

TABLE 5

SPECIFICITY OF HSV-1 PRIMERS AND PROBES

| SAMPLE # | COMMENTS | APAI GEL INTER-PRETATION | HSV-1GG (MOTA) | HSV-1GG (PAT) |
|---|---|---|---|---|
| 0-2053 | previously untyped | HSV-2 | 680 | 0 |
| 0-1753 | previously untyped | No Product | 90 | 0 |
| D-8575 | previously untyped | HSV-2 | 390 | 0 |
| C5 (S?) | previously untyped | HSV-2 | 150 | 0 |
| July-67 | previously untyped | HSV-2 | 740 | 0 |
| ATCC VR-734 | ATCC | HSV-2 | 30 | 0 |
| ATCC VR-540 | ATCC | HSV-2 | 100 | 0 |
| Clin11 | Quest Diagnostics | HSV-2 | 410 | 0 |

TABLE 5-continued

SPECIFICITY OF HSV-1 PRIMERS AND PROBES

| SAMPLE # | COMMENTS | APAI GEL INTER-PRETATION | HSV-1GG (MOTA) | HSV-1GG (PAT) |
|---|---|---|---|---|
| Clin12 | Quest Diagnostics | HSV-2 | 20 | 0 |
| Clin13 | Quest Diagnostics | HSV-2 | 290 | 0 |
| Clin14 | Quest Diagnostics | HSV-2 | 320 | 0 |
| Clin15 | Quest Diagnostics | HSV-2 | 40 | 0 |
| Clin16 | Quest Diagnostics | HSV-2 | 210 | 0 |
| Clin17 | Quest Diagnostics | HSV-2 | 10 | 0 |
| Clin18 | Quest Diagnostics | HSV-2 | 40 | 0 |
| Clin19 | Quest Diagnostics | HSV-1* | 145050 | 53.38 |
| Clin20 | Quest Diagnostics | HSV-2 | 220 | 0 |

*Clin19 was typed as HSV-2 by Quest and typed HSV-1 by ApaI analysis.

TABLE 6

SPECIFICITY OF HSV-1 PRIMERS AND PROBES

| Organism | Strain # | HSV-1GG (MOTA) | HSV-1GG SDA (PAT) |
|---|---|---|---|
| Adenovirus-5 | ABI 74-070 | 180 | 0 |
| Candida albicans | ATCC 44808 | 0 | 0 |
| Cryptococcus neoformans | ATCC 36556 | 60 | 0 |
| Cytomegalovirus (AD-169) | ABi 68-125 | 10 | 0 |
| Enterovirus (Echovirus-11) | ABi 74-084 | 20 | 0 |
| Epstein-Barr virus | SIGMA 104HO854 | 240 | 0 |
| Escherichia coli | ATCC 11775 | 0 | 0 |
| Fusobacterium nucleatum | ATCC 25586 | 0 | 0 |
| Group B Streptococcus | ATCC 12386 | 130 | 0 |
| Hameophilus influenzae | ATCC 33533 | 320 | 0 |
| Listeria moncytogenes | ATCC 7644 | 40 | 0 |
| Mycoplasma pneumoniae | ATCC 63-030 | 300 | 0 |
| Neisseria meningitidis | ATCC 13077 | 10 | 0 |
| Propioibacterium acnes | ATCC 6919 | 0 | 0 |
| Pseudomonas aeruginosa | ATCC 27853 | 170 | 0 |
| Resp. Synctial virus | ABi 74-093 | 180 | 0 |
| Staphylococcus. Aureus | ATCC 25923 | 0 | 0 |
| Staphylococcus epidermidis | ATCC E155 | 0 | 0 |
| Streptococcus mitis | ATCC 6249 | 10 | 0 |
| Streptococcus mutans | ATCC 25175 | 20 | 0 |
| Streptococcus pneumoniae | ATCC 6303 | 0 | 0 |
| Streptococcus pyogenes | ATCC 19615 | 0 | 0 |
| Rhiniovirus | Clin 74 | 250 | 0 |

ATCC—American Type Culture Collection;
ABi—Advanced Biotechnologies, Inc.

Example 6

Cloning of HSV-2 Glycoprotein-G SDA Target Region

PCR was performed on DNA from the HSV-2 strain ATCC VR-540 using the primers HSV2PCRR and HSV2PCRL with an annealing temperature of 69° C. These primers amplify a 254 base pair fragment within the Glycoprotein G (US4) gene of HSV-2. Amplified DNA was inserted into a pUC18 plasmid vector (Invitrogen). The recombinant clone was dubbed pHSV2-NT #9-1. Plasmid DNA was purified and linearized by digestion with BamHI restriction enzyme. The DNA was purified using QIAGEN QIAquick spin columns and quantified by analysis with fluorescent Picogreen® reagent. Dilutions of the target DNA for future experiments were prepared in water containing 7ng/µL salmon sperm DNA.

Example 7

Amplification of Cloned HSV-2 DNA

The analytical sensitivity of the DNA amplification assay was estimated using dilutions of the cloned plasmid. Eight replicate SDA reactions were performed at each target level using systems 2.0 and 5.2. These eight reactions were equivalent to 500, 250, 100, 50, 25, 10 and 0 copies of double stranded DNA per reaction. Amplification was conducted at 52° C. using a BD ProbeTec™ ET instrument with 50 nM each of HSV2GGLB1.0 and HSV2GGRB1.0, 100 nM of HSV2GGLP1.0, 500 nM HSV2GGRP2.0 or 5.2, 250 nM HSV2GGAD1.0, 500 nM MPC.D/R. The sequences of these primers are listed in Table 2. Final buffer conditions were as follows: 71 mM Bicine, 56.6 mM KOH, 23.9 mM KPO4, 15.4% DMSO, 5 mM magnesium acetate, 500 mM 2'-deoxycytosine-5-o-(1-thiotriphosphate)(dCsTP), 100 nM each of dATP, dGTP and dTTP, 100 µg/µL BSA, approximately 3.515 units of Bst polymerase and approximately 30 units of BsoBI restriction endonuclease.

Fluorescence was monitored for 60 passes over the course of one hour. Results were expressed in terms of area under the curve or "MOTA" score, and as PAT scores (Passes After Threshold). For the purpose of the present invention, MOTA scores greater than or equal to 3500 and PAT scores greater than 0 were considered "positive." The lowest level of HSV2GG target DNA at which the assay yielded 100% positive results was at 50 copies per reaction for both systems 2.0 and 5.2. Seven of eight replicates were positive for system 2.0 at 25 copies, and six of eight were positive for system 5.2 at 25 copies.

Example 8

Detection of HSV-2 Virus Particles by SDA

To verify the ability of the primers and probes of the invention to detect HSV-2, SDA was performed on two strains of HSV-2 obtained from American Type Culture Collection (ATCC), nine strains obtained from Quest Diagnostic (Baltimore, Md.) and five strains from Ohio State University (OSU) typed as HSV-2 by ApaI analysis.

The strains from OSU were characterized by amplifying a region of the DNA polymerase gene by PCR. One set of PCR primers was designed to amplify the same region in both HSV-1 and HSV-2. The two types of virus were distinguishable by the presence of an ApaI restriction endonuclease recognition site in the HSV-2 PCR fragment that is not present in PCR products generated from strains of HSV-1. When incubated with the ApaI restriction enzyme, the HSV-2 derived PCR products are cleaved into two shorter fragments while those obtained from HSV-1 remain intact. Restricted fragments were resolved on agarose gel electrophoresis with appropriate controls.

The concentrations of the viral stocks used to evaluate the SDA system were not known. The viral stocks were diluted 1:10 in phosphate buffered saline and 10 µL of this suspension was tested in SDA. Results are shown in Table 7. All strains of HSV-2 were detected using the amplification primers from systems 1.0, 2.0 and 5.2, demonstrating the ability of disclosed primers and probes to detect strains of HSV1 from a diversity of sources.

TABLE 7

STRAINS OF HSV-2 TESTED IN THE HSV2GG SYSTEMS

| STRAIN | DILUTION FROM STOCK | HSV2GG 1.0 MOTA | HSV2GG 1.0 PAT | HSV2GG 2.0 MOTA | HSV2GG 2.0 PAT | HSV2GG 5.2 MOTA | HSV2GG 5.2 PAT |
|---|---|---|---|---|---|---|---|
| OSU 0-2053 | 1:10 | 5460 | 34 | 103902 | 52.2 | 104334 | 52.6 |
| OSU D-8575 | 1:10 | 59950 | 50 | 123676 | 52.6 | 129392 | 52.7 |
| OSU C5 | 1:10 | 34230 | 47 | 96845 | 52.4 | 103945 | 52.6 |
| OSU 7-2667 | 1:10 | 135900 | 53 | 88932 | 52.4 | 86426 | 52.6 |
| ATCC VR-734 | 1.58E+9 TCID/μL | 173220 | 54 | 108624 | 52.4 | 105501 | 52.6 |
| ATCC VR-540 | 1.58E+4 TCID/μL | 183190 | 55 | 131364 | 52.5 | 128644 | 52.6 |
| Quest Clin 11 | 1:10 | 157930 | 52 | 83950 | 52.4 | 86787 | 52.5 |
| Quest Clin 12 | 1:10 | 127670 | 51 | 129929 | 52.3 | 122640 | 52.4 |
| Quest Clin 13 | 1:10 | 136710 | 51 | 103652 | 52.2 | 101533 | 52.4 |
| Quest Clin 14 | 1:10 | 135660 | 53 | 106922 | 52.2 | 110146 | 52.5 |
| Quest Clin 15 | 1:10 | 8440 | 38 | 110309 | 51.1 | 141752 | 52.2 |
| Quest Clin 16 | 1:10 | 157960 | 53 | 125560 | 52.1 | 133232 | 52.4 |
| Quest Clin 17 | 1:10 | 203550 | 53 | 85670 | 51.4 | 81501 | 52.2 |
| Quest Clin 18 | 1:10 | 64690 | 48 | 153890 | 52.1 | 154132 | 52.4 |
| Quest Clin 20 | 1:10 | 225400 | 54 | 142087 | 52.4 | 119663 | 52.5 |

OSU = Ohio State University;
ATCC = American Type Culture Collection;
Quest = Quest Diagnostics

Example 9

Specificity of SDA for HSV-2 DNA

Twenty-five strains of HSV-1 were tested with HSV2GG SDA systems 1.0, 2.0 and 5.2. Ten microliters of each suspension of the HSV-1 dilution were added per reaction. None of the 25 strains were detected by the HSV-2 systems. Results are shown in Table 8. In addition, a panel of other microorganisms was tested using the primers and probes of the disclosed invention method. These microorganisms included bacteria, yeast and other viruses likely to be encountered in clinical specimens. None of the organisms tested positive for HSV-2. Results are shown in Table 9.

TABLE 8

SPECIFICITY FOR HSV-2 STRAINS AGAINST HSV-1 STRAINS IN THE HSV2GG SYSTEMS

| HSV-1 Strain | Dilution from Stock | HSV2 GG 1.0 MOTA | HSV2 GG 1.0 PAT | HSV2 GG 2.0 MOTA | HSV2 GG 2.0 PAT | HSV2 GG 5.2 MOTA | HSV2 GG 5.2 PAT |
|---|---|---|---|---|---|---|---|
| 0-2021 | 1:10 | 250 | 0 | 2059 | 0 | 433 | 0 |
| 0-450 | 1:10 | 150 | 0 | 500 | 0 | 632 | 0 |
| 0-1010 | 1:10 | 580 | 0 | 1063 | 0 | 1733 | 0 |
| OSU0-2526 | 1:10 | 330 | 0 | 988 | 0 | 816 | 0 |
| OSU0-1753 | 1:10 | 250 | 0 | 16 | 0 | 4 | 0 |
| OSUD-8-1973 | 1:10 | 90 | 0 | 1 | 0 | 433 | 0 |
| OSU7-370 | 1:10 | 110 | 0 | 612 | 0 | 102 | 0 |
| OSU0116-3 | 1:10 | 290 | 0 | 25 | 0 | 45 | 0 |
| OSU1136 | 1:10 | 390 | 0 | 88 | 0 | 61 | 0 |
| OSUA.P. | 1:10 | 470 | 0 | No data | No data | No data | No data |
| ATCC 260VR | 2.8E+6 TCID/μL | 610 | 0 | 656 | 0 | 858 | 0 |
| ATCC VR-733 | 15.8 TCID/μL | 1270 | 0 | No data | No data | No data | No data |
| ATCC VR-735 | 15.8 TCID/μL | 130 | 0 | 0 | 0 | 1008 | 0 |

TABLE 8-continued

SPECIFICITY FOR HSV-2 STRAINS AGAINST HSV-1 STRAINS IN THE HSV2GG SYSTEMS

| HSV-1 Strain | Dilution from Stock | HSV2 GG 1.0 MOTA | HSV2 GG 1.0 PAT | HSV2 GG 2.0 MOTA | HSV2 GG 2.0 PAT | HSV2 GG 5.2 MOTA | HSV2 GG 5.2 PAT |
|---|---|---|---|---|---|---|---|
| ATCC VR-539 | 1000 vp/μL | 480 | 0 | 926 | 0 | 1429 | 0 |
| Quest Clin 1 | 1:10 | 990 | 0 | 1011 | 0 | 64 | 0 |
| Quest Clin 2 | 1:10 | 190 | 0 | 0 | 0 | 68 | 0 |
| Quest Clin 3 | 1:10 | 790 | 0 | 419 | 0 | 75 | 0 |
| Quest Clin 4 | 1:10 | 310 | 0 | No data | No data | No data | No data |
| Quest Clin 5 | 1:10 | 580 | 0 | 311 | 0 | 212 | 0 |
| Quest Clin 6 | 1:10 | 370 | 0 | 0 | 0 | 0 | 0 |
| Quest Clin 7 | 1:10 | 380 | 0 | 369 | 0 | 0 | 0 |
| Quest Clin 8 | 1:10 | 520 | 0 | 1576 | 0 | 62 | 0 |
| Quest Clin 9 | 1:10 | 770 | 0 | 2300 | 0 | 1138 | 0 |
| Quest Clin 10 | 1:10 | 440 | 0 | 1956 | 0 | 1500 | 0 |
| Quest Clin 19 | 1:10 | 640 | 0 | 587 | 0 | 480 | 0 |

OSU = Ohio State University;
ATCC = American Type Culture Collection;
Quest = Quest Diagnostics

TABLE 9

SPECIFICITY FOR HSV-2 AGAINST VARIOUS BACTERIA, VIRUSES AND YEASTS USING THE HSV2GG SYSTEMS

| Organism | HSV2 GG 1.0 MOTA | HSV2 GG 1.0 PAT | HSV2 GG 2.0 MOTA | HSV2 GG 2.0 PAT | HSV2 GG 5.2 MOTA | HSV2 GG 5.2 PAT |
|---|---|---|---|---|---|---|
| Adenovirus-5 | 50 | 0 | 0 | 0 | 581 | 0 |
| Candida albicans | 530 | 0 | 0 | 0 | 246 | 0 |
| Cryptococcus neoformans | 120 | 0 | 1344 | 0 | 1436 | 0 |
| Cytomegalovirus (AD-169) | 140 | 0 | 3 | 0 | 1 | 0 |
| Enterovirus (Echovirus-11) | 680 | 0 | 491 | 0 | 15 | 0 |
| Epstein-Barr virus | 530 | 0 | No data | No data | No data | No data |
| Escherichia coli | 20 | 0 | 1974 | 0 | 69 | 0 |
| Fusobacterium nucleatum | 0 | 0 | 801 | 0 | 1560 | 0 |
| Group B Streptococcus | 180 | 0 | 0 | 0 | 387 | 0 |
| Haemophilus influenzae | 340 | 0 | 618 | 0 | 1675 | 0 |
| Pseudomonas aeruginosa | 500 | 0 | 183 | 0 | 1303 | 0 |
| Respiratory Synctial Virus | 350 | 0 | 4 | 0 | 236 | 0 |
| Staphylococcus aureus | 30 | 0 | 885 | 0 | 551 | 0 |
| Staphylococcus epidermidis | 10 | 0 | 84 | 0 | 831 | 0 |
| Streptococcus mitis | 190 | 0 | 8 | 0 | 226 | 0 |
| Streptococcus mutans | 510 | 0 | 294 | 0 | 1813 | 0 |
| Streptococcus pneumoniae | 60 | 0 | 404 | 0 | 2006 | 0 |
| Streptococcus pyogenes | 0 | 0 | 1063 | 0 | 3149 | 0 |
| Listeria monocytogenes | 470 | 0 | 984 | 0 | 0 | 0 |
| Mycoplasma pneumoniae | 530 | 0 | 16 | 0 | 408 | 0 |
| Neisseria meningitides | 300 | 0 | 1661 | 0 | 134 | 0 |
| Propionibacterium acnes | 40 | 0 | 1559 | 0 | 1022 | 0 |

TABLE 9-continued

SPECIFICITY FOR HSV-2 AGAINST VARIOUS BACTERIA,
VIRUSES AND YEASTS USING THE HSV2GG SYSTEMS

| Organism | HSV2 GG 1.0 MOTA | HSV2 GG 1.0 PAT | HSV2 GG 2.0 MOTA | HSV2 GG 2.0 PAT | HSV2 GG 5.2 MOTA | HSV2G G 5.2 PAT |
|---|---|---|---|---|---|---|
| Rhinovirus | 20 | 0 | No data | No data | No data | No data |
| Rhinovirus 74 | 0 | 0 | No data | No data | No data | No data |
| Rhinovirus 114 | 60 | 0 | No data | No data | No data | No data |
| HIV-1 | 430 | 0 | 1335 | 0 | 2795 | 0 |

What is claimed is:

1. A polynucleotide comprising a sequence consisting essentially of a target binding sequence of any one of SEQ ID NOs: 38, 43, 45, and 50.

2. The polynucleotide of claim 1, further comprising a sequence needed for an amplification reaction to proceed.

3. The polynucleotide of claim 1, further comprising a sequence selected from the group consisting of a hairpin, a g-quartet, a restriction enzyme recognition site, an RNA polymerase promoter, and a sequence that binds to an assay probe.

4. The polynucleotide of claim 1, wherein the polynucleotide is labeled with a detectable label.

5. The polynucleotide of claim 4, wherein the label is a fluorescent moiety.

6. A kit for detecting a sequence, comprising one or more primers having a sequence consisting essentially of a target binding sequence of any one of SEQ ID NOs: 38, 43, 45, and 50, and adapter primers, wherein the adapter primers are selected from the group consisting of: SEQ ID NOs: 44-45.

7. The kit of claim 6, further comprising bumper primers.

8. The kit of claim 7, wherein the bumper primers are selected from the group consisting of: SEQ ID NOs: 46-47.

9. The kit of claim 6, further comprising detector primers.

10. The kit of claim 9, wherein the detector primers are selected from the group consisting of: SEQ ID NOs: 30-35.

11. The polynucleotide of claim 5, wherein the fluorescent moiety comprises a donor and quencher dye pair selected from the group consisting of: fluorescein (FAM)/rhodamine (ROX); FAM/P-(dimethyl aminophenylazo) benzoic acid (DABCYL); ROX/DABCYL; fluorescein isothiocyanate (FITC)/tetramethylrhodamine isothiocyanate (TRITC); FITC/Texas Red™; FITC/N-hydroxysuccinimidyl 1-pyrenebutyrate (PYB); FITC/eosin isothiocyanate (EITC); N-hydroxysuccinimidyl 1-pentanesulfonate (PYS)/FITC; FITC/Rhodamine X; and FITC/tetramethylrhodamine (TAMRA).

12. The kit of claim 6, further comprising:
(a) an adapter primer sequence capable of hybridizing to the target sequence through a target binding sequence located at the 3' end of the adapter primer, wherein the adapter primer comprises a 5' generic tail, and the adapter primer is selected from the group consisting of: SEQ ID NOs: 19-22; and
(b) a detector primer sequence capable of hybridizing to the complement of the 5' tail of the adapter primer through the 3' portion of the detector primer, wherein the detector primer sequence comprises a 5' restriction enzyme recognition site and a detectable label selected from the group consisting of: a fluorescent moiety, a radioisotope, a chemiluminescent agent, an enzyme substrate capable of developing a visible reaction product, and a ligand-detectably labeled ligand binding partner.

13. The kit of claim 12, wherein the detector primer sequence comprises a structural moiety selected from the group consisting of: a hairpin and g-quartet.

14. The kit of claim 12, wherein the detectable label is a fluorescent moiety.

15. The kit of claim 14, wherein the fluorescent moiety comprises a donor and quencher dye pair selected from the group consisting of: fluorescein (FAM)/rhodamine (ROX); FAM/P-(dimethyl aminophenylazo) benzoic acid (DABCYL); ROX/DABCYL; fluorescein isothiocyanate (FITC)/tetramethylrhodamine isothiocyanate (TRITC); FITC/Texas Red™; FITC/N-hydroxysuccinimidyl 1-pyrenebutyrate (PYB); FITC/eosin isothiocyanate (EITC); N-hydroxysuccinimidyl 1-pentanesulfonate (PYS)/FITC; FITC/Rhodamine X; and FITC/tetramethylrhodamine (TAMRA).

16. The kit of claim 12, wherein the detector primer is selected from the group consisting of: SEQ ID NOs: 30-35.

17. A method of detecting the presence of HSV-2 target sequence in a sample, said method comprising:
    (a) adding the sample to a first amplification primer of SEQ ID NO: 38; and a second amplification primer of SEQ ID NO:43, producing an amplified HSV-2 nucleic acid product; and
    (b) detecting the amplified HSV-2 nucleic acid product, wherein the detection of the amplified product indicates the presence of HSV-2 in the sample.

18. The method of claim 17, wherein the amplified HSV-2 nucleic acid product is detected by a method selected from the group consisting of: universal detection, gel electrophoresis, and quantitative hybridization.

19. The method of claim 17, further comprising
    (c) adding the sample to a first bumper primer of SEQ ID NO: 46 and a second bumper of SEQ ID NO: 47.

20. The method of claim 19, wherein the detecting step further comprises,
    (d) hybridizing the first amplification primer and an adapter primer selected from the group consisting of: SEQ ID NOs: 44-45 to the amplified HSV-2 target sequence, wherein the adapter primer hybridizes downstream of the first amplification primer;
    (e) extending the 3' ends of the first amplification primer and the adapter primer producing an adapter primer extension product, wherein the extension of the first amplification primer displaces the adapter primer extension product;
    (f) hybridizing the second amplification primer to the adapter primer extension product;
    (g) extending the 3' end of the second amplification primer, producing a double-stranded molecule comprising the adapter primer extension product and its complement, wherein each strand comprises a nickable restriction enzyme site;
    (h) nicking the double-stranded molecule, creating a 5' portion and a 3' portion, wherein the 5' portion comprises a nicked tail and the 3' portion comprises a nicked complement adapter primer extension product;
    (i) extending 3' end of the nicked tail, displacing the nicked complement adapter primer extension product, wherein the displaced nicked complement adapter primer extension product is single-stranded;
    (j) hybridizing a detector primer to the complement adapter primer extension product, wherein the detector primer comprises a detectable label;
    (k) extending the 3' ends of the detector primer and the complement adapter primer extension product, producing a double-stranded detection molecule comprising a detector primer extension product and its complement, wherein each strand comprises a cleavable restriction enzyme recognition site;
    (l) cleaving the double-stranded detection molecule; and
    (m) detecting the detectable label.

21. The method of claim 20, wherein the detectable label is a fluorescent moiety.

22. The method of claim 21, wherein the fluorescent moiety comprises a donor and quencher dye pair selected from the group consisting of: fluorescein (FAM)/rhodamine (ROX); FAM/P-(dimethyl aminophenylazo) benzoic acid (DABCYL); ROX/DABCYL; fluorescein isothiocyanate (FITC)/tetramethylrhodamine isothiocyanate (TRITC); FITC/Texas Red™; FITC/N-hydroxysuccinimidyl 1-pyrenebutyrate (PYB); FITC/eosin isothiocyanate (EITC); N-hydroxysuccinimidyl 1-pentanesulfonate (PYS)/FITC; FITC/Rhodamine X; and FITC/tetramethylrhodamine (TAMRA).

23. The method of claim 22, wherein the detector primer is selected from the group consisting of: SEQ ID NOs: 30-35.

24. The method of claim 20, further comprising:
    (n) amplifying an internal amplification control (IAC) target sequence selected from the group consisting of: SEQ ID NOs: 47-48;
    (o) hybridizing the first amplification primer and an IAC adapter primer selected from the group consisting of: SEQ ID NOs: 50-51 to the IAC, wherein the adapter primer hybridizes downstream of the first amplification primer;
    (p) extending the 3' ends of the first amplification primer and the IAC adapter primer, producing an IAC adapter primer extension product, wherein the extension of the first amplification primer displaces the IAC adapter primer extension product;
    (q) hybridizing the second amplification primer to the IAC adapter primer extension product;
    (r) extending the 3' end of the second amplification primer, producing a double-stranded molecule comprising the IAC adapter primer extension product and its complement, wherein each strand comprises a nickable restriction enzyme site;
    (s) nicking the double-stranded molecule, creating a 5' portion and a 3' portion, wherein the 5' portion comprises a nicked tail and the 3' portion comprises a nicked complement IAC adapter primer extension product;
    (t) extending the 3' end of the nicked tail, displacing the nicked complement IAC adapter primer extension product, wherein the displaced nicked complement adapter primer extension product is single-stranded;
    (u) hybridizing an IAC detector primer to the single-stranded complement IAC adapter primer extension product, wherein the IAC detector primer comprises a detectable label and detects the IAC target sequence;
    (v) extending the 3' ends of the IAC detector primer and the complement IAC adapter primer extension product, producing a double-stranded detection molecule comprising a detector primer extension product and its complement, wherein each strand comprises a cleavable restriction enzyme site;

(w) cleaving the double-stranded detection molecule; and (x) detecting the detectable label.

25. The method of claim 24, wherein the IAC detector primer sequence is selected from the group consisting of: SEQ ID NOs: 34-35; and the detector primer for detecting HSV-2 target sequence is selected from the group consisting of SEQ ID NOs: 30-33.

26. The method of claim 25, wherein the detectable label is a fluorescent moiety.

27. The method of claim 26, wherein the fluorescent moiety comprises a donor and quencher dye pair selected from the group consisting of: fluorescein (FAM)/rhodamine (ROX); FAM/P-(dimethyl aminophenylazo) benzoic acid (DABCYL); ROX/DABCYL; fluorescein isothiocyanate (FITC)/tetramethylrhodamine isothiocyanate (TRITC); FITC/Texas Red™; FITC/N-hydroxysuccinimidyl 1-pyrenebutyrate (PYB); FITC/eosin isothiocyanate (EITC); N-hydroxysuccinimidyl 1-pentanesulfonate (PYS)/FITC; FITC/Rhodamine X; and FITC/tetramethylrhodamine (TAMRA).

28. The method of claim 24, wherein the detector primer is selected from the group consisting of: SEQ ID NOs: 30-35.

29. A composition comprising primers for the detection of an HSV-2 target sequence in a sample by an amplification reaction comprising:
(a) a first amplification primer sequence that hybridizes to the HSV-2 target sequence, wherein the first amplification primer sequence is SEQ ID NO: 38;
(b) a second amplification primer sequence that hybridizes to a complement of the HSV-2 target sequence, wherein the second amplification primer is selected from the group consisting of: SEQ ID NOs: 39-43;
(c) a first bumper primer sequence that hybridizes to the HSV-2 target sequence upstream of the first amplification primer, wherein the first bumper primer is SEQ ID NO: 46; and
(d) a second bumper primer sequence that hybridizes to a complement of the HSV-2 target sequence upstream of the second amplification primer, wherein the second amplification primer is SEQ ID NO: 47.

30. A method for detecting, in a sample, an HSV-2 target sequence, comprising:
(e) hybridizing a first amplification primer of SEQ ID NO: 38 to the HSV-2 target sequence;
(f) hybridizing a first bumper primer of SEQ ID NO: 46 to the HSV-2 target sequence, wherein the first bumper primer hybridizes to the HSV-2 target sequence upstream of the first amplification primer and the second bumper primer hybridizes to the complement target sequence upstream of the second amplification primer;
(g) extending the 3' ends of the first bumper primer and the first amplification primer, producing a first amplification primer extension product, wherein the extension of the first bumper primer displaces the first amplification primer extension product;
(h) hybridizing a second amplification primer, having a sequence selected from the group consisting of SEQ ID NOs: 39-43, to the first amplification primer extension product;
(i) hybridizing a second bumper primer of SEQ ID NO: 47 to the first amplification primer extension product;
(j) extending the 3' ends of the second bumper primer and the second amplification primer, producing a second amplification primer extension product, wherein the extension of the second bumper primer displaces the second amplification primer extension product;

(k) hybridizing the first amplification primer to the second amplification primer extension product, (l) extending the 3' end of the first amplification primer of step (g), producing a double-stranded molecule comprising the second amplification primer extension product and its complement, wherein each strand comprises a nickable restriction enzyme site;

(m) nicking the double-stranded molecule, creating a 5' portion and a 3' portion, wherein the 5' portion comprises a nicked tail and the 3' portion comprises a nicked second amplification primer extension product, and its complement;

(n) extending the 3' nicked tail, displacing the nicked second amplification primer extension product, wherein the nicked complement second amplification primer extension product is single-stranded;

(o) extending the 3' end of the nicked tail, displacing the nicked complement second amplification primer extension product, wherein the nicked complement second amplification primer extension product is single-stranded;

(p) exponentially amplifying the two single-stranded molecules by separately hybridizing the first amplification primer and the second amplification primer to each single-stranded molecule, and repeating steps (h)-(k), thereby amplifying the HSV-2 target sequence; and (q) detecting the amplified HSV-2 target sequence.

31. The composition of claim 29, wherein the first amplification primer sequence and/or the second amplification primer sequence further comprises a hairpin, a g-quartet, a restriction enzyme recognition site, an RNA polymerase promoter, or a sequence that binds to an assay probe.

32. A method of detecting a Herpes Simplex Virus type 2 (HSV-2) target sequence comprising:
hybridizing the polynucleotide of claim 17 to the HSV-2 target sequence; and
detecting the HSV-2 target sequence.

33. A method of detecting a target sequence comprising:
(a) amplifying the target sequence using a first amplification primer comprising a sequence consisting essentially of a target binding sequence of SEQ ID NO:38;
(b) amplifying the target sequence using a second amplification primer comprising a sequence consisting essentially of a target binding sequence of SEQ ID NO:43; and
(c) detecting the amplified target sequence.

34. The method of detecting a target sequence of claim 33, wherein said target sequence is a Herpes Simplex Virus type 2 (HSV-2) target sequence.

35. The method of claim 33, wherein the amplification reaction is a Strand Displacement Amplification (SDA) reaction.

36. The method of claim 33, wherein the detection method is selected from the group consisting of: direct detection, Polymerase Chain Reaction (PCR), Ligase Chain Reaction (LCR), in situ hybridization, Transcription Mediated Amplification (TMA), Self-Sustaining Sequence Replication (3SR), Rolling Circle Amplification (RCA), Qβ replicase system, and Nucleic Acid Sequence Based Amplification (NASBA).

37. The method of claim 33, wherein the first amplification primer further comprises a sequence selected from the group consisting of: a hairpin, a g-quartet, a restriction enzyme recognition sequence, and a sequence that binds to an assay probe.

38. The method of claim 33, wherein the first amplification primer further comprises a detectable label.

39. The method of claim 38, wherein the label is a fluorescent moiety.

40. The method of claim 33, wherein the first amplification primer comprises a sequence selected from the group consisting of a restriction enzyme recognition site and a RNA polymerase promoter.

41. The method of claim 33, further comprising amplifying an Internal Amplification Control (IAC).

42. The method of claim 41, wherein the IAC is selected from the group consisting of: SEQ ID NOs: 26-27 and 48-49.

43. The method of claim 41, further comprising detecting amplified IAC.

44. The method of claim 43, wherein the amplified IAC is detected by a means different from the amplified target sequence.

45. A method of detecting a Herpes Simplex Virus type 2 (HSV-2) target sequence comprising:
(a) hybridizing one or more polynucleotides, wherein the one or more polynucleotides comprise a sequence consisting essentially of a target binding sequence of SEQ ID NO:38 or SEQ ID NO:43;
(b) and detecting the HSV-2 target sequence.

46. The method of claim 45, wherein said one or more polynucleotides further comprises a detectable label.

47. The method of claim 46, wherein the detectable label is a fluorescent moiety.

* * * * *

SEQUENCE LISTING

<160> NUMBER OF SEQ ID NOS: 55

<210> SEQ ID NO 1
<211> LENGTH: 756
<212> TYPE: DNA
<213> ORGANISM: human herpes virus-1
<220> FEATURE:
<221> NAME/KEY: misc_feature
<223> OTHER INFORMATION: Glycoprotein G (US 4) gene
<220> FEATURE:
<221> NAME/KEY: misc_feature
<222> LOCATION: (284)..(285)
<223> OTHER INFORMATION: Insert XXX, where X= no base

<400> SEQUENCE: 1

```
aaaaagaccc cgacccgcgt ctgtggtgtt tttggcatca tgtcgccggg cgccatgcgt      60
gccgttgttc ccattatccc attccttttg gttcttgtcg gtgtatcggg ggttcccacc     120
aacgtctcct ccaccaccca accccaactc cagaccaccg gtcgtccctc gcatgaagcc     180
cccaacatga cccagaccgg caccaccgac tctcccaccg ccatcagcct taccacgccc     240
gaccacacac cccccatgcc aagtatcgga ctggaggagg aggaagagga ggaggggcc      300 ggggacggcg aacatcttga ggggggagat gggacccgtg acaccctacc ccagtccccg     360
ggcccagcct tcccgttggc tgaggacgtc gagaaggaca acccaaccg tcccgtagtc      420 ccatcccccg atcccaacaa ctcccccgcg cgccccgaga ccagtcgccc gaagacaccc     480
cccaccatta tcgggccgct ggcaactcgc cccacgaccc gactcacctc aaagggacga     540
cccttggttc cgacgcctca acatacccccg ctgttctcgt tcctcactgc ctcccccgcc     600
ctggacaccc tcttcgtcgt cagcaccgtc atccacacct tatcgttttt gtgtattggt     660
gcgatggcga cacctgtg tggcggttgg tccagacgcg ggcgacgcac acacctagc       720 gtgcgttacg tgtgcctgcc gtccgaacgc gggtag                              756
```

<210> SEQ ID NO 2
<211> LENGTH: 717
<212> TYPE: DNA
<213> ORGANISM: Human Herpes Simplex Virus -1

<400> SEQUENCE: 2

```
atgtcgcagg gcgccatgcg tgccgttgtt cccattatcc cattcctttt ggttcttgtc      60
ggtgtatcgg gggttcccac caacgtctcc tccaccaccc aacccaact ccagaccacc     120 ggtcgtccct cgcatgaagc ccccaacatg acccagaccg gcaccaccga ctctcccacc     180
gccatcagcc ttaccacgcc cgaccacaca ccccccatgc caagtattgg actggaggag     240
gaggaagagg aggaggggc cggggacggc gaacatcttg agggggaga tgggacccgt      300
```

```
gacaccctac cccagtcccc gggcccagcc ttcccgttgg ctgaggacgt cgagaaggac      360
aaacccaacc gtcccgtagt cccatccccc gatcccaaca actcccccgc gcgccccgag      420
accagtcgcc cgaagacacc ccccaccatt atcgggccgc tggcaactcg ccccacgacc      480
cgactcacct caaagggacg acccttggtt ccgacgcctc aacataccccc gctgttctcg     540 ttcctcactg cctcccccgc cctggacacc ctcttcgtcg tcagcaccgt catccacacc      600
ttatcgtttt tgtgtattgg tgcgatggcg acacacctgt gtggcggttg tccagacgc       660 gggcgacgca cacaccctag cgtgcgttac gtgtgcctgc cgtccgaacg cgggtag        717
```

<210> SEQ ID NO 3
<211> LENGTH: 1071
<212> TYPE: DNA
<213> ORGANISM: Human Herpes Simplex Virus -2
<220> FEATURE:
<221> NAME/KEY: misc_feature
<223> OTHER INFORMATION: Glycoprotein (US4) gene fragment

<400> SEQUENCE: 3

```
ctcatggcct tgaccgagga cgcgtcctcc gattcgccta cgtccgctcc ggagaagacg       60
cccctccctg tgtcggccac cgccatggcg ccctcagtcg acccaagcgc ggaaccgacc      120
gcccccgcaa ccactactcc ccccgacgag atggccacac aagccgcaac ggtcgccgtt      180
acgccggagg aaacggcagt cgcctccccg cccgcgactg catccgtgga gtcgtcgcca      240
ccccccgccg cggcggcaac gcccggggcc gggcacacga acaccagcag cgcctccgca      300
gcgaaaacgc cccccaccac accagccccc acgaccccccc cgcccacgtc tacccacgcg      360 acccccccgcc ccacgactcc ggggccccaa acaacccctc ccggacccgc aaccccgggt      420
ccggtgggcg cctccgccgc gcccacggcc gattccccccc tcaccgcctc gccccccgct      480
accgcgccgg ggccctcggc cgccaacgtt tcggtcgccg cgaccaccgc cacgcccgga      540
acccggggca ccgcccgtac cccccaacg gacccaaaga cgcacccaca cggacccgcg       600
gacgctcccc ccggctcgcc agccccccca ccccccgaac atcgcggcgg acccgaggag      660
tttgagggcg ccggggacgg cgaacccccc gaggacgacg acagcgccac cggcctcgcc      720
ttccgaactc cgaaccccaa caaaccaccc ccgcgcgcc ccgggcccat ccgccccacg      780
ctcccgccag gaattcttgg gccgctcgcc cccaacacgc ctcgcccccc cgcccaagct      840
cccgctaagg acatgccctc gggcccaca ccccaacaca tccccctgtt ctggttccta       900
acggcctccc ctgctctaga tatcctcttt atcatcagca ccaccatcca cacggcggcg      960
ttcgtttgtc tggtcgcctt ggcagcacaa cttttggcgcg ccgggcggg gcgcaggcga     1020 tacgcgcacc cgagcgtgcg ttacgtatgt ctgccacccg agcgggatta g              1071
```

<210> SEQ ID NO 4
<211> LENGTH: 390
<212> TYPE: DNA
<213> ORGANISM: Human Herpes Simplex Virus -2

<400> SEQUENCE: 4

```
accaccccccc gcgcgccccg ggcccatccg ccccacgctc ccgccaggaa ttcttgggcc       60
gctcgccccc aacacgcctc gcccccccgc ccaagctccc gctaaggaca tgccctcggg      120
ccccacaccc caacacatcc cctgttctg gttcctaacg gcctcccctg ctctagatat       180
cctctttatc atcagcacca ccatccacac ggcggcgttc gtttgtctgg tcgccttggc      240
agcacaactt tggcgcggcc gggcggggcg caggcgatac gcgcacccga gcgtgcgtta      300
```
cgtatgtctg ccacccgagc gggattaggg ggtgggggtg gggggcgaga aacgatgaag    360
gacgggaaag ggaacagcga ccaaatgtca                                      390

<210> SEQ ID NO 5
<211> LENGTH: 22
<212> TYPE: DNA
<213> ORGANISM: Human Herpes Simplex Virus -1
<220> FEATURE:
<221> NAME/KEY: misc_feature
<223> OTHER INFORMATION: PCRL1.0

<400> SEQUENCE: 5
gcggaattcg acccttggtt cc                                              22

<210> SEQ ID NO 6
<211> LENGTH: 22
<212> TYPE: DNA
<213> ORGANISM: Human Herpes Simplex Virus -1
<220> FEATURE:
<221> NAME/KEY: misc_feature
<223> OTHER INFORMATION: PCRR1.0

<400> SEQUENCE: 6
gcgggatccc caaccaccac ac                                              22

<210> SEQ ID NO 7
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1GGLP1.0- SDA PRIMER

<400> SEQUENCE: 7
accgcatcga atgactgtct cgggctgttc tcgttcctc                            39

<210> SEQ ID NO 8
<211> LENGTH: 38
<212> TYPE: DNA
<213> ORGANISM: Human Herpes Simplex Virus -1
<220> FEATURE:
<221> NAME/KEY: misc_feature
<223> OTHER INFORMATION: HSV1GGLP1.1- SDA PRIMER

<400> SEQUENCE: 8
accgcatcga atgactgtct cgggctgttc tcgttcct                             38

<210> SEQ ID NO 9
<211> LENGTH: 40
<212> TYPE: DNA
<213> ORGANISM: Human Herpes Simplex Virus -1
<220> FEATURE:
<221> NAME/KEY: misc_feature
<223> OTHER INFORMATION: HSV1GGRP1.0- SDA PRIMER

<400> SEQUENCE: 9
cgattccgct ccagacttct cgggcaccaa tacacaaaaa                           40

<210> SEQ ID NO 10
<211> LENGTH: 40
<212> TYPE: DNA
<213> ORGANISM: Human Herpes Simplex Virus -1
<220> FEATURE:
<221> NAME/KEY: misc_feature
<223> OTHER INFORMATION: HSV1GGRP1.0- SDA PRIMER

```
<400> SEQUENCE: 10
cgattccgct ccagacttct cgggcaacaa tacacacaaa                    40

<210> SEQ ID NO 11
<211> LENGTH: 41
<212> TYPE: DNA
<213> ORGANISM: Human Herpes Simplex Virus -1
<220> FEATURE:
<221> NAME/KEY: misc_feature
<223> OTHER INFORMATION: HSV1GGRP2.0- SDA PRIMER

<400> SEQUENCE: 11
cgattccgct ccagacttct cgggcaccaa tacacaaaaa c                  41

<210> SEQ ID NO 12
<211> LENGTH: 41
<212> TYPE: DNA
<213> ORGANISM: Human Herpes Simplex Virus -1
<220> FEATURE:
<221> NAME/KEY: misc_feature
<223> OTHER INFORMATION: HSV1GGRP2.1- SDA PRIMER

<400> SEQUENCE: 12
cgattccgct ccagacttct cgggcaacaa tacacacaaa c                  41

<210> SEQ ID NO 13
<211> LENGTH: 42
<212> TYPE: DNA
<213> ORGANISM: Human Herpes Simplex Virus -1
<220> FEATURE:
<221> NAME/KEY: misc_feature
<223> OTHER INFORMATION: HSV1GGRP3.0- SDA primer

<400> SEQUENCE: 13
cgattccgct ccagacttct cgggcaccaa tacacaaaaa cg                 42

<210> SEQ ID NO 14
<211> LENGTH: 42
<212> TYPE: DNA
<213> ORGANISM: Human Herpes Simplex Virus -1
<220> FEATURE:
<221> NAME/KEY: misc_feature
<223> OTHER INFORMATION: HSV1GGRP3.1- SDA primer

<400> SEQUENCE: 14
cgattccgct ccagacttct cgggcaacaa tacacacaaa cg                 42

<210> SEQ ID NO 15
<211> LENGTH: 41
<212> TYPE: DNA
<213> ORGANISM: Human Herpes Simplex Virus -1
<220> FEATURE:
<221> NAME/KEY: misc_feature
<223> OTHER INFORMATION: HSV1GGRP4.0- SDA primer

<400> SEQUENCE: 15
cgattccgct ccagacttct cgggcaatac acaaaaacga t                  41

<210> SEQ ID NO 16
<211> LENGTH: 41
<212> TYPE: DNA
<213> ORGANISM: Human Herpes Simplex Virus -1
<220> FEATURE:
<221> NAME/KEY: misc_feature
<223> OTHER INFORMATION: HSV1GGRP4.1- SDA primer

<400> SEQUENCE: 16
```
cgattccgct ccagacttct cgggcaatac acacaaacga t        41

<210> SEQ ID NO 17
<211> LENGTH: 41
<212> TYPE: DNA
<213> ORGANISM: Human Herpes Simplex Virus -1
<220> FEATURE:
<221> NAME/KEY: misc_feature
<223> OTHER INFORMATION: HSV1GGRP4.2- SDA primer

<400> SEQUENCE: 17
cgattccgct ccagacttct cgggcaatac acacaaatga t        41

<210> SEQ ID NO 18
<211> LENGTH: 38
<212> TYPE: DNA
<213> ORGANISM: Human Herpes Simplex Virus -1
<220> FEATURE:
<221> NAME/KEY: misc_feature
<223> OTHER INFORMATION: HSV1GGRP5.2- SDA primer

<400> SEQUENCE: 18
cgattccgct ccagacttct cgggaaggtg tggatgac        38

<210> SEQ ID NO 19
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1GGAD1.0- Adapter primer

<400> SEQUENCE: 19
acgttagcca ccatacggat ccgtcatcca caccttatc        39

<210> SEQ ID NO 20
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1GGAD2.1- Adapter primer

<400> SEQUENCE: 20
acgttagcca ccatacggat ggacaccctc ttcgtcgtc        39

<210> SEQ ID NO 21
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1GGAD3.0- Adapter primer

<400> SEQUENCE: 21
acgttagcca ccatacttga ggacaccctc ttcgtcgtc        39

<210> SEQ ID NO 22
<211> LENGTH: 37
<212> TYPE: DNA
<213> ORGANISM: Human Herpes Simplex Virus -1
<220> FEATURE:
<221> NAME/KEY: misc_feature
<223> OTHER INFORMATION: HSV1GGAD3.1- Adapter primer

<400> SEQUENCE: 22

```
acgttagcca ccatacttga ggacaccctc ttcgtcg                              37
```

<210> SEQ ID NO 23
<211> LENGTH: 15
<212> TYPE: DNA
<213> ORGANISM: Human Herpes Simplex Virus -1
<220> FEATURE:
<221> NAME/KEY: misc_feature
<223> OTHER INFORMATION: HSV1GGLB1.0- Bumper primer

<400> SEQUENCE: 23

```
gacgcctcaa catac                                                     15
```

<210> SEQ ID NO 24
<211> LENGTH: 14
<212> TYPE: DNA
<213> ORGANISM: Human Herpes Simplex Virus -1
<220> FEATURE:
<221> NAME/KEY: misc_feature
<223> OTHER INFORMATION: HSV1GGRB1.0- Bumper primer

<400> SEQUENCE: 24

```
gtgtgtcgcc atcg                                                      14
```

<210> SEQ ID NO 25
<211> LENGTH: 14
<212> TYPE: DNA
<213> ORGANISM: Human Herpes Simplex Virus -1
<220> FEATURE:
<221> NAME/KEY: misc_feature
<223> OTHER INFORMATION: HSV1GGLB1.1- Bumper primer

<400> SEQUENCE: 25

```
aggtgtgtcg ccat                                                      14
```

<210> SEQ ID NO 26
<211> LENGTH: 71
<212> TYPE: DNA
<213> ORGANISM: Human Herpes Simplex Virus -1
<220> FEATURE:
<221> NAME/KEY: misc_feature
<223> OTHER INFORMATION: HSV1IAC8.1- IAC target sequence

<400> SEQUENCE: 26

```
ctgttctcgt tcctcactgc ctcccccgcc ctggacaccc tcttgctgct gagcaccgtc    60
atccacacct t                                                         71
```

<210> SEQ ID NO 27
<211> LENGTH: 71
<212> TYPE: DNA
<213> ORGANISM: Human Herpes Simplex Virus -1
<220> FEATURE:
<221> NAME/KEY: misc_feature
<223> OTHER INFORMATION: HSV1IAC8.7- IAC target sequence

<400> SEQUENCE: 27

```
ctgttctcgt tcctcactgc ctcccccgcc ctggacaccc tctgttcatc tagcaccgtc    60
atccacacct t                                                         71
```

<210> SEQ ID NO 28
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1IACAD8.1- IAC adapter primer

```
<400> SEQUENCE: 28
actgatccgc actaacgact ggacaccctc ttgctgctg                    39

<210> SEQ ID NO 29
<211> LENGTH: 39
<212> TYPE: DNA
<213> ORGANISM: Human Herpes Simplex Virus -1
<220> FEATURE:
<221> NAME/KEY: misc_feature
<223> OTHER INFORMATION: HSV1IACAD8.7- IAC adapter primer

<400> SEQUENCE: 29
actgatccgc actaacgact ggacaccctc tgttcatct                    39

<210> SEQ ID NO 30
<211> LENGTH: 35
<212> TYPE: DNA
<213> ORGANISM: ARTIFICIAL
<220> FEATURE:
<223> OTHER INFORMATION: Synthetic detector primer
<220> FEATURE:
<221> NAME/KEY: misc_feature
<223> OTHER INFORMATION: TBD10.2 D/R- Detector primer
<220> FEATURE:
<221> NAME/KEY: misc_feature
<222> LOCATION: (1)..(1)
<223> OTHER INFORMATION: DABCYL
<220> FEATURE:
<221> NAME/KEY: misc_feature
<222> LOCATION: (6)..(11)
<223> OTHER INFORMATION: BsoBI restriction enzyme recognition site
<220> FEATURE:
<221> NAME/KEY: misc_feature
<222> LOCATION: (15)..(15)
<223> OTHER INFORMATION: ROX

<400> SEQUENCE: 30
tagcgcccga gcgctacgtt agccaccata cggat                        35

<210> SEQ ID NO 31
<211> LENGTH: 29
<212> TYPE: DNA
<213> ORGANISM: ARTIFICIAL
<220> FEATURE:
<223> OTHER INFORMATION: Synthetic detector primer
<220> FEATURE:
<221> NAME/KEY: misc_feature
<223> OTHER INFORMATION: TBD15 D/R- Detector primer
<220> FEATURE:
<221> NAME/KEY: misc_feature
<222> LOCATION: (1)..(1)
<223> OTHER INFORMATION: DABCYL
<220> FEATURE:
<221> NAME/KEY: misc_feature
<222> LOCATION: (3)..(8)
<223> OTHER INFORMATION: BsoBI restriction enzyme recognition site
<220> FEATURE:
<221> NAME/KEY: misc_feature
<222> LOCATION: (9)..(9)
<223> OTHER INFORMATION: ROX

<400> SEQUENCE: 31
tgcccgagta cgttagccac catacggat                               29

<210> SEQ ID NO 32
<211> LENGTH: 28
<212> TYPE: DNA
<213> ORGANISM: ARTIFICIAL
<220> FEATURE:
<223> OTHER INFORMATION: Synthetic detector primer
```

```
<220> FEATURE:
<221> NAME/KEY: misc_feature
<223> OTHER INFORMATION: TBD16 (D/R)- Detector primer
<220> FEATURE:
<221> NAME/KEY: misc_feature
<222> LOCATION: (1)..(1)
<223> OTHER INFORMATION: DABCYL
<220> FEATURE:
<221> NAME/KEY: misc_feature
<222> LOCATION: (3)..(7)
<223> OTHER INFORMATION: BsoBI restriction enzyme recognition site
<220> FEATURE:
<221> NAME/KEY: misc_feature
<222> LOCATION: (8)..(8)
<223> OTHER INFORMATION: ROX

<400> SEQUENCE: 32
tcccgagtac gttagccacc atacggat                                   28

<210> SEQ ID NO 33
<211> LENGTH: 29
<212> TYPE: DNA
<213> ORGANISM: ARTIFICIAL
<220> FEATURE:
<223> OTHER INFORMATION: Synthetic detector primer
<220> FEATURE:
<221> NAME/KEY: misc_feature
<223> OTHER INFORMATION: MPC.DR- Detector primer
<220> FEATURE:
<221> NAME/KEY: misc_feature
<222> LOCATION: (1)..(1)
<223> OTHER INFORMATION: DABCYL
<220> FEATURE:
<221> NAME/KEY: misc_feature
<222> LOCATION: (3)..(8)
<223> OTHER INFORMATION: BsoBI restriction enzyme recognition site
<220> FEATURE:
<221> NAME/KEY: misc_feature
<222> LOCATION: (9)..(9)
<223> OTHER INFORMATION: ROX

<400> SEQUENCE: 33
tccccgagta cgttagccac catacttga                                  29

<210> SEQ ID NO 34
<211> LENGTH: 29
<212> TYPE: DNA
<213> ORGANISM: ARTIFICIAL
<220> FEATURE:
<223> OTHER INFORMATION: Synthetic detector primer
<220> FEATURE:
<221> NAME/KEY: misc_feature
<223> OTHER INFORMATION: MPC2.FD- Detector primer
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (3)..(8)
<223> OTHER INFORMATION: BsoBI restriction enzyme recognition site
<220> FEATURE:
<221> NAME/KEY: misc_feature
<222> LOCATION: (9)..(9)
<223> OTHER INFORMATION: DABCYL dye

<400> SEQUENCE: 34
tccccgagta ctgatccgca ctaacgact                                  29

<210> SEQ ID NO 35
<211> LENGTH: 28
<212> TYPE: DNA
<213> ORGANISM: ARTIFICIAL
```

```
<220> FEATURE:
<223> OTHER INFORMATION: Synthetic detector primer
<220> FEATURE:
<221> NAME/KEY: misc_feature
<223> OTHER INFORMATION: AltD8 (F/D)- Detector primer
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (3)..(7)
<223> OTHER INFORMATION: BsoBI restriction enzyme recognition site

<400> SEQUENCE: 35
acccgagtag ctatccgcca taagccat                                       28

<210> SEQ ID NO 36
<211> LENGTH: 23
<212> TYPE: DNA
<213> ORGANISM: Human Herpes Simplex Virus -2
<220> FEATURE:
<221> NAME/KEY: misc_feature
<223> OTHER INFORMATION: HSV2PCRL- PCR primer

<400> SEQUENCE: 36
gcggaattca ttcttgggcc gct                                            23

<210> SEQ ID NO 37
<211> LENGTH: 23
<212> TYPE: DNA
<213> ORGANISM: Human Herpes Simplex Virus -2
<220> FEATURE:
<221> NAME/KEY: misc_feature
<223> OTHER INFORMATION: HSV2PCRR- PCR primer

<400> SEQUENCE: 37
gcgggatcca cgtaacgcac gct                                            23

<210> SEQ ID NO 38
<211> LENGTH: 39
<212> TYPE: DNA
<213> ORGANISM: Human Herpes Simplex Virus -2
<220> FEATURE:
<221> NAME/KEY: misc_feature
<223> OTHER INFORMATION: HSV2GGLP1.0- SDA primer

<400> SEQUENCE: 38
accgcatcga atgactgtct cgggctgttc tggttccta                           39

<210> SEQ ID NO 39
<211> LENGTH: 40
<212> TYPE: DNA
<213> ORGANISM: Human Herpes Simplex Virus -2
<220> FEATURE:
<221> NAME/KEY: misc_feature
<223> OTHER INFORMATION: HSV2GGRP1.0- SDA primer

<400> SEQUENCE: 39
cgattccgct ccagacttct cgggcgacca gacaaacgaa                          40

<210> SEQ ID NO 40
<211> LENGTH: 39
<212> TYPE: DNA
<213> ORGANISM: Human Herpes Simplex Virus -2
```

```
<220> FEATURE:
<221> NAME/KEY: misc_feature
<223> OTHER INFORMATION: HSV2GGRP1.1- SDA primer

<400> SEQUENCE: 40
cgattccgct ccagacttct cgggaccaga caaacgaac                              39

<210> SEQ ID NO 41
<211> LENGTH: 41
<212> TYPE: DNA
<213> ORGANISM: Human Herpes Simplex Virus -2
<220> FEATURE:
<221> NAME/KEY: misc_feature
<223> OTHER INFORMATION: HSV2GGRP1.2- SDA primer

<400> SEQUENCE: 41
cgattccgct ccagacttct cgggcgacca gacaaacgaa c                          41

<210> SEQ ID NO 42
<211> LENGTH: 37
<212> TYPE: DNA
<213> ORGANISM: Human Herpes Simplex Virus -2
<220> FEATURE:
<221> NAME/KEY: misc_feature
<223> OTHER INFORMATION: HSV2GGRP2.0- SDA primer

<400> SEQUENCE: 42
cgattccgct ccagacttct cgggaacgcc gccgtgt                                37

<210> SEQ ID NO 43
<211> LENGTH: 37
<212> TYPE: DNA
<213> ORGANISM: Human Herpes Simplex Virus -2
<220> FEATURE:
<221> NAME/KEY: misc_feature
<223> OTHER INFORMATION: HSV2GGRP5.2- SDA primer

<400> SEQUENCE: 43
cgattccgct ccagacttct cgggccgtgt ggatggt                                37

<210> SEQ ID NO 44
<211> LENGTH: 39
<212> TYPE: DNA
<213> ORGANISM: Human Herpes Simplex Virus -2
<220> FEATURE:
<221> NAME/KEY: misc_feature
<223> OTHER INFORMATION: HSV2GGAD1.0- Adapter primer

<400> SEQUENCE: 44
acgttagcca ccatacggat ccaccatcca cacggcggc                              39

<210> SEQ ID NO 45
<211> LENGTH: 44
<212> TYPE: DNA
<213> ORGANISM: Human Herpes Simplex Virus -2
<220> FEATURE:
<221> NAME/KEY: misc_feature
<223> OTHER INFORMATION: HSV2GGAD2.0- Adapter primer

<400> SEQUENCE: 45
acgttagcca ccatacttga tgctctagat atcctcttta tcat                        44

<210> SEQ ID NO 46
<211> LENGTH: 15
<212> TYPE: DNA
<213> ORGANISM: Human Herpes Simplex Virus -2
<220> FEATURE:
```

<221> NAME/KEY: misc_feature
<223> OTHER INFORMATION: HSV2GGLB1.0- Bumper primer

<400> SEQUENCE: 46
cacaccccaa cacat                                              15

<210> SEQ ID NO 47
<211> LENGTH: 14
<212> TYPE: DNA
<213> ORGANISM: Human Herpes Simplex Virus -2
<220> FEATURE:
<221> NAME/KEY: misc_feature
<223> OTHER INFORMATION: HSV2GGRB1.0- Bumper primer

<400> SEQUENCE: 47
ttgtgctgcc aagg                                               14

<210> SEQ ID NO 48
<211> LENGTH: 70
<212> TYPE: DNA
<213> ORGANISM: Human Herpes Simplex Virus -2
<220> FEATURE:
<221> NAME/KEY: misc_feature
<223> OTHER INFORMATION: HSV2-IAC 5.2A1- IAC target sequence

<400> SEQUENCE: 48
ctgttctggt tcctaacggc ctcccctgct ctagatatcc tctttactac cagcaccacc      60
atccacacgg                                                            70

<210> SEQ ID NO 49
<211> LENGTH: 70
<212> TYPE: DNA
<213> ORGANISM: Human Herpes Simplex Virus -2
<220> FEATURE:
<221> NAME/KEY: misc_feature
<223> OTHER INFORMATION: HSV2-IAC 5.2A2- IAC target sequence

<400> SEQUENCE: 49
ctgttctggt tcctaacggc ctcccctgct ctagatatcc tcttaactac cagcaccacc      60
atccacacgg                                                            70

<210> SEQ ID NO 50
<211> LENGTH: 44
<212> TYPE: DNA
<213> ORGANISM: Human Herpes Simplex Virus -2
<220> FEATURE:
<221> NAME/KEY: misc_feature
<223> OTHER INFORMATION: HSV2GG IAC ADA1.0- IAC Adapter primer

<400> SEQUENCE: 50
actgatccgc actaacgact tgctctagat atcctcttta ctac                      44

<210> SEQ ID NO 51
<211> LENGTH: 43
<212> TYPE: DNA
<213> ORGANISM: Human Herpes Simplex Virus -2
<220> FEATURE:
<221> NAME/KEY: misc_feature
<223> OTHER INFORMATION: HSV2GG IAC ADA2.0- IAC Adapter primer

<400> SEQUENCE: 51
actgatccgc actaacgact tgctctagat atcctcttaa cta                       43

<210> SEQ ID NO 52
<211> LENGTH: 6

-continued

```
<212> TYPE: DNA
<213> ORGANISM: Bacillus stearothermophilus
<220> FEATURE:
<221> NAME/KEY: misc_feature
<223> OTHER INFORMATION: BsoBI restriction enzyme recognition site

<400> SEQUENCE: 52 ctcggg                                                                      6

<210> SEQ ID NO 53
<211> LENGTH: 6
<212> TYPE: DNA
<213> ORGANISM: Bacillus stearothermophilus
<220> FEATURE:
<221> NAME/KEY: misc_feature
<223> OTHER INFORMATION: BsoBI restriction enzyme recognition site

<400> SEQUENCE: 53 cccggg                                                                      6

<210> SEQ ID NO 54
<211> LENGTH: 6
<212> TYPE: DNA
<213> ORGANISM: Bacillus stearothermophilus
<220> FEATURE:
<221> NAME/KEY: misc_feature
<223> OTHER INFORMATION: BsoBI restriction enzyme recognition site

<400> SEQUENCE: 54 ctcgag                                                                      6

<210> SEQ ID NO 55
<211> LENGTH: 6
<212> TYPE: DNA
<213> ORGANISM: Bacillus stearothermophilus
<220> FEATURE:
<221> NAME/KEY: misc_feature
<223> OTHER INFORMATION: BsoBI restriction enzyme recognition site

<400> SEQUENCE: 55 cccgag                                                                      6
```